United States Patent [19]
Collins et al.

[11] Patent Number: 6,096,728
[45] Date of Patent: Aug. 1, 2000

[54] COMPOSITION AND METHOD FOR TREATING INFLAMMATORY DISEASES

[75] Inventors: David S. Collins, Lafayette; Michael P. Bevilacqua, Boulder, both of Colo.

[73] Assignee: Amgen Inc., Thousand Oaks, Calif.

[21] Appl. No.: 08/798,414

[22] Filed: Feb. 7, 1997

Related U.S. Application Data

[60] Provisional application No. 60/011,419, Feb. 9, 1996, and provisional application No. 60/032,789, Dec. 6, 1996.

[51] Int. Cl.⁷ .............................. A61K 31/70; C07K 1/00
[52] U.S. Cl. .............................................. 514/62; 530/351
[58] Field of Search ................................ 514/62; 530/351

[56] References Cited

U.S. PATENT DOCUMENTS

| | | | |
|---|---|---|---|
| 4,784,991 | 11/1988 | Nimrod et al. | 514/62 |
| 4,808,576 | 2/1989 | Schultz et al. | 514/54 |
| 5,858,355 | 1/1999 | Glorioso et al. | 424/93.21 |

FOREIGN PATENT DOCUMENTS

| | | |
|---|---|---|
| 9173636 | 10/1991 | Australia . |
| WO 92/11359 | 7/1992 | WIPO . |
| WO 93/07863 | 4/1993 | WIPO . |

OTHER PUBLICATIONS

Thomas, Robert C.; Interleukin–1 receptor antagonist(IL–1ra) as a probe and as a atreatment for IL–1 mediated disease; Int. J. Immunopharmac., vol. 14. No. 3, pp. 475–480, 1992.

*Primary Examiner*—Theodore J. Criares
*Attorney, Agent, or Firm*—Thomas D. Zindrick; Steven M. Odre; Ron K. Levy

[57] ABSTRACT

A pharmaceutical composition comprising (a) an effective amount of controlled release polymer and (b) an effective amount of a proteinaceous IL-1 inhibitor. The composition exhibits a therapeutic effect on inflammation and is useful for treating IL-1 mediated inflammatory diseases, particularly diseases of the joint.

20 Claims, 5 Drawing Sheets

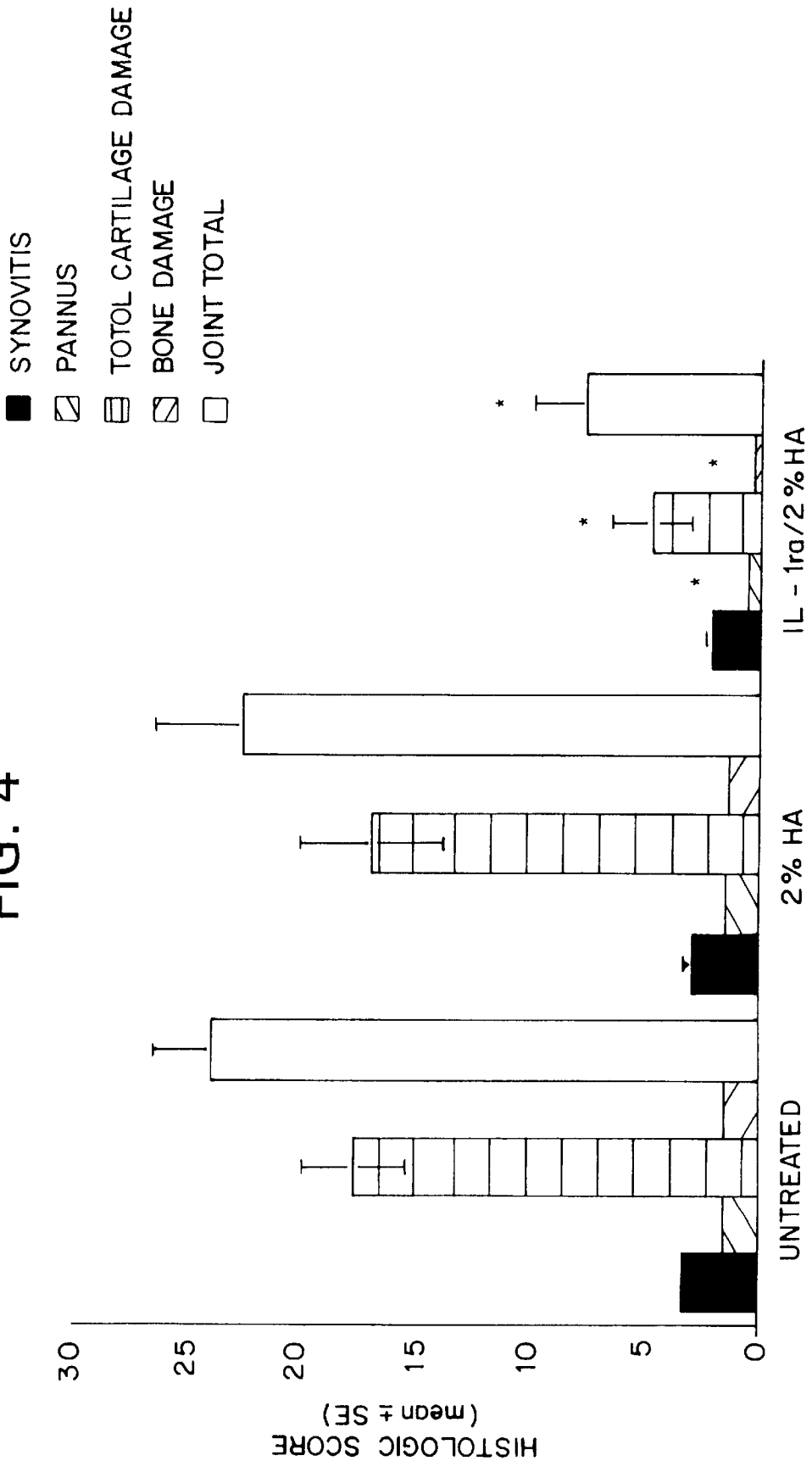

FIG. 5

```
     ATGCGACCCTCTGGGAGAAATCCAGCAAGATGCAAGCCTTCAGAATCTGGGATGTTAAC
1    ------+---------+---------+---------+---------+---------+   60
     M  R  P  S  G  R  K  S  S  K  M  Q  A  F  R  I  W  D  V  N

CAGAAGACCTTCTATCTGAGGAACAACCAACTAGTTGCTGGATACTTGCAAGGACCAAAT
61   ------+---------+---------+---------+---------+---------+  120
     Q  K  T  F  Y  L  R  N  N  Q  L  V  A  G  Y  L  Q  G  P  N

GTCAATTTAGAAGAAAAGATAGATGTGGTACCCATTGAGCCTCATGCTCTGTTCTTGGGA
121  ------+---------+---------+---------+---------+---------+  180
     V  N  L  E  E  K  I  D  V  V  P  I  E  P  H  A  L  F  L  G

ATCCATGGAGGGAAGATGTGCCTGTCCTGTGTCAAGTCTGGTGATGAGACCAGACTCCAG
181  ------+---------+---------+---------+---------+---------+  240
     I  H  G  G  K  M  C  L  S  C  V  K  S  G  D  E  T  R  L  Q

CTGGAGGCAGTTAACATCACTGACCTGAGCGAGAACAGAAGCAGGACAAGCGCTTCGCC
241  ------+---------+---------+---------+---------+---------+  300
     L  E  A  V  N  I  T  D  L  S  E  N  R  K  Q  D  K  R  F  A

TTCATCCGCTCAGACAGTGGCCCCACCACCAGTTTTGAGTCTGCCGCCTGCCCCGGTTGG
301  ------+---------+---------+---------+---------+---------+  360
     F  I  R  S  D  S  G  P  T  T  S  F  E  S  A  A  C  P  G  W

TTCCTCTGCACAGCGGATGGAAGCTGACCCGTCAGCCTCACCAATATGCCTGACGAA
361  ------+---------+---------+---------+---------+---------+  420
     F  L  C  T  A  M  E  A  D  Q  P  V  S  L  T  N  M  P  D  E

GGCGTCATGGTCACCAAATTCTACTTCCAGGAGGACGAGTAG
421  ------+---------+---------+---------+--    462
     G  V  M  V  T  K  F  Y  F  Q  E  D  E  *
```

COMPOSITION AND METHOD FOR TREATING INFLAMMATORY DISEASES

This is a nonprovisional Application derived from U.S. provisional applications Ser. Nos. 60/011,419, filed Feb. 9, 1996; 60/032,789, filed Dec. 6, 1996; and Attorney Docket #A-365B-P (serial # not yet available), filed Jan. 23, 1997.

FIELD OF THE INVENTION

The present invention relates to the field of inflammation. More specifically, the present invention relates to a composition for the purpose of preventing or treating inflammatory diseases.

BACKGROUND OF THE INVENTION

Inflammation is the body's defense reaction to injuries such as those caused by mechanical damage, infection or antigenic stimulation. An inflammatory reaction may be expressed pathologically when inflammation is induced by an inappropriate stimulus such as an autoantigen, is expressed in an exaggerated manner or persists well after the removal of the injurious agents.

While the etiology of inflammation is poorly understood, considerable information has recently been gained regarding the molecular aspects of inflammation. This research has led to identification of certain cytokines which are believed to figure prominently in the mediation of inflammation. Cytokines are extracellular proteins that modify the behavior of cells, particularly those cells that are in the immediate area of cytokine synthesis and release. One of the most potent inflammatory cytokines yet discovered and a cytokine which is thought to be a key mediator in many diseases and medical conditions is interleukin-1 (IL-1). IL-1, which is manufactured (though not exclusively) by cells of the macrophage/monocyte lineage, may be produced in two forms: IL-1 alpha (IL-1α) and IL-1 beta (IL-1β).

A disease or medical condition is considered to be an "interleukin-1 mediated disease" if the spontaneous or experimental disease or medical condition is associated with elevated levels of IL-1 in bodily fluids or tissue or if cells or tissues taken from the body produce elevated levels of IL-1 in culture. In many cases, such interleukin-1 mediated diseases are also recognized by the following additional two conditions: (1) pathological findings associated with the disease or medical condition can be mimicked experimentally in animals by the administration of IL-1; and (2) the pathology induced in experimental animal models of the disease or medical condition can be inhibited or abolished by treatment with agents which inhibit the action of IL-1. In most interleukin-1 mediated diseases at least two of the three conditions are met, and in many interleukin-1 mediated diseases all three conditions are met. A non-exclusive list of acute and chronic interleukin-1 (IL-1)-mediated inflammatory diseases includes but is not limited to the following: acute pancreatitis; ALS; Alzheimer's disease; cachexia/anorexia; asthma; atherosclerosis; chronic fatigue syndrome, fever; diabetes (e.g., insulin diabetes); glomerulonephritis; graft versus host rejection; hemohorragic shock; hyperalgesia, inflammatory bowel disease; inflammatory conditions of a joint, including osteoarthritis, psoriatic arthritis and rheumatoid arthritis; ischemic injury, including cerebral ischemia (e.g., brain injury as a result of trauma, epilepsy, hemorrhage or stroke, each of which may lead to neurodegeneration); lung diseases (e.g., ARDS); multiple myeloma; multiple sclerosis; myelogenous (e.g., AML and CML) and other leukemias; myopathies (e.g., muscle protein metabolism, esp. in sepsis); osteoporosis; Parkinson's disease; pain; pre-term labor; psoriasis; reperfusion injury; septic shock; side effects from radiation therapy, temporal mandibular joint disease, tumor metastasis; or an inflammatory condition resulting from strain, sprain, cartilage damage, trauma, orthopedic surgery, infection or other disease processes.

Inflammatory conditions of a joint are chronic joint diseases that afflict and disable, to varying degrees, millions of people worldwide. Rheumatoid arthritis is a disease of articular joints in which the cartilage and bone are slowly eroded away by a proliferative, invasive connective tissue called pannus, which is derived from the synovial membrane. The disease may involve peri-articular structures such as bursae, tendon sheaths and tendons as well as extra-articular tissues such as the subcutis, cardiovascular system, lungs, spleen, lymph nodes, skeletal muscles, nervous system (central and peripheral) and eyes (Silberberg (1985), *Anderson's Pathology,* Kissane (ed.), II:1828). Osteoarthritis is a common joint disease characterized by degenerative changes in articular cartilage and reactive proliferation of bone and cartilage around the joint. Osteoarthritis is a cell-mediated active process that may result from the inappropriate response of chondrocytes to catabolic and anabolic stimuli. Changes in some matrix molecules of articular cartilage reportedly occur in early osteoarthritis (Thonar et al. (1993), *Rheumatic disease clinics of North America,* Moskowitz (ed.), 19:635–657 and Shinmei et al. (1992), *Arthritis Rheum.,* 35:1304–1308).

It is believed that rheumatoid arthritis results from the presentation of a relevant antigen to an immunogenetically susceptible host. The antigens that could potentially initiate an immune response that results in rheumatoid arthritis might be endogenous or exogenous. Possible endogenous antigens include collagen, mucopolysaccharides and rheumatoid factors. Exogenous antigens include mycoplasms, mycobacteria, spirochetes and viruses. By-products of the immune reaction inflame the synovium (i.e., prostaglandins and oxygen radicals) and trigger destructive joint changes (i.e., collagenase).

There is a wide spectrum of disease severity, but many patients run a course of intermittent relapses and remissions with an overall pattern of slowly progressive joint destruction and deformity. The clinical manifestations may include symmetrical polyarthritis of peripheral joints with pain, tenderness, swelling and loss of function of affected joints; morning stiffness; and loss of cartilage, erosion of bone matter and subluxation of joints after persistent inflammation. Extra-articular manifestations include rheumatoid nodules, rheumatoid vasculitis, pleuropulmonary inflammations, scleritis, sicca syndrome, Felty's syndrome (splenomegaly and neutropenia), osteoporosis and weight loss (Katz (1985), *Am. J. Med.,* 79:24 and Krane and Simon (1986), *Advances in Rheumatology,* Synderman (ed.), 70(2) :263–284). The clinical manifestations result in a high degree of morbidity resulting in disturbed daily life of the patient.

The involvement of interleukin-1 in arthritis has been implicated by two distinct lines of evidence. First, increased levels of interleukin-1, and of the mRNA encoding it, have been found in the synovial tissue and fluid of arthritic joints. See, for example, Buchan et al., "Third Annual General Meeting of the British Society for Rheumatology," London, England, Nov. 19–21, 1988, *J. Rheumatol.,* 25(2); Fontana et al. (1982), *Rheumatology Int.,* 2:49–53; and Duff et al. (1988), *Monokines and Other Non-Lymphocytic Cytokines,* M. Powanda et al. (eds), pp. 387–392 (Alan R. Liss, Inc.).

Second, the administration of interleukin-1 to healthy joint tissue has been shown on numerous occasions to result in the erosion of cartilage and bone. In one experiment, intra-articular injections of IL-1 into rabbits were shown to cause cartilage destruction in vivo (Pettipher et al. (1986), *Proc. Nat'l Acad. Sci. U.S.A.*, 83:8749–8753). In other studies, IL-1 was shown to cause the degradation of both cartilage and bone in tissue explants (Saklatavala et al. (1987), *Development of Diseases of Cartilage and Bone Matrix*, Sen and Thornhill (eds.), pp. 291–298 (Alan R. Liss, Inc.) and Stashenko et al. (1987), *The American Association of Immunologists*, 183:1464–1468). One generally accepted theory which is used to explain the causal link between IL-1 and arthritis is that IL-1 stimulates various cell types, such as fibroblasts and chondrocytes, to produce and secrete proinflammatory or degradative compounds such as prostaglandin $E_2$ and metalloproteinases.

Interleukin-1 receptor antagonist (IL-1ra) is a human protein that acts as a natural inhibitor of interleukin-1. IL-1 receptor antagonist (IL-1ra) has been disclosed as a potential agent for use in the clinical treatment of IL-1 mediated diseases (Australian Patent No. 649245). However, IL-1ra has a relatively short half-life. It therefore would be advantageous to administer IL-1ra in a sustained release formulation to treat IL-1 mediated diseases.

Hyaluronic acid is a naturally occurring mucopolysaccharide consisting of residues of D-glucoronic acid and N-acetyl-D-glucosamine in an unbranched chain. The polymer has an average molecular weight of $(5-6) \times 10^6$ and exhibits excellent biocompatibility. In the articular cartilage, hyaluronic acid plays an important role in the construction of the cartilage matrix by aggregating with proteoglycan. Furthermore, it has been reported that under pathological conditions such as rheumatoid arthritis, osteoarthritis and infectious arthritis, the concentrations and molecular weight of hyaluronic acid in the joint are changed and cause changes in the nature of the synovial fluid.

Both chemical cross-linking and derivatization have been used to enhance its rheological properties or increase the degradation time of certain drugs (Cortivo et al. (1991), *Biomaterials*, 2:727–730; Benedetti et al. (1990), *J. Controlled Release*, 13:33–41 and Hunt et al. (1990), *J. Controlled Release*, 12:159–169).

It has been shown that the injection of high molecular weight hyaluronic acid derivatives may restore the damaged hyaluronic acid layer on the articular cartilage surface and may be effective for treating some kinds of articular conditions in clinical and fundamental tests. Examples of scientific publications describing such use of hyaluronic acid derivatives for treatment of articular conditions include Nizolek & White (1981), *Cornell Vet.*, 71:355–375; Namiki et al. (1982), *Int. J. Chem. Pharmacol., Therapy and Toxicol.*, 20:501–507; Asheim and Lindblad (1976), *Acta Vet Scand*, 17(4):379–394; Svanstrom (1978), *Proceedings of the 24th Annual Convention of the American Association of Equine Practitioners*, St Louis, Mo., p. 345–348; Wigren et al. (1975), *Upsala J Med Sci Suppl*, 17:1–20; and Gingerich et al. (1980), *Res Vet Sci*, 30:192–197. An exemplary scientific publication describing the use of hyaluronic acid both alone and with cortisone in various animal joints, especially horses, is Rydell et al. (1971), *Clinical Orthopaedics and Related Research*, 80:25–32. The use of hyaluronic acid in human joints is reported by Peyron et al. (1974), *Pathologie Biologie*, 22(8):731–736. The intra-articular use of hyaluronic acid in horse joints has been commercially promoted in connection with Pharmacia's Hylartil™ and Hylartin V™ products and Sterivet's Synacid™ product. However, although symptoms such as pain and stiffness become a serious problem in the treatment of joint diseases, hyaluronic acid does not directly improve such symptoms.

Additionally, hyaluronic acid has been used for drug delivery. In one study, microspheres prepared from hyaluronic acid esters were used for the nasal delivery of insulin (Illum et al. (1994), *J. Controlled Release*, 29:133–141). Blank spheres were prepared by an emulsification/solvent evaporation technique, exposed to an insulin solution for an hour, and then lyophilized. When administered to sheep, the mean bioavailability was found to be 11% when compared with insulin administered by the subcutaneous route. This system has also been used as a delivery device for nerve growth factor (Ghezzo et al. (1992), *Int. J. Pharm.*, 87:21–29). However, it has been reported that when certain hyaluronic acid compositions were admixed with the albumin, they enhanced the clearance rate of that protein from the synovial space (Myers and Brandt (1995), *J. Rheumatol.*, 22:1732–1739), suggesting that a combination of hyaluronic acid with a protein, such as IL-1ra, would be no more effective than hyaluronic acid alone in the treatment of inflammatory diseases, particularly when administered via intrarticular injection.

It is an objective of the present invention to provide therapeutic methods and compositions for the treatment of IL-1 mediated inflammatory diseases. This and other objects of the present invention will become apparent from the description hereinafter.

SUMMARY OF THE INVENTION

This invention relates to a pharmaceutical composition comprising a controlled release polymer (e.g., hyaluronan) and a proteinaceous IL-1 inhibitor (e.g., IL-1ra) as an agent for treating IL-1 mediated inflammatory diseases. The type of treatment herein referred to is intended for mammals, including humans.

BRIEF DESCRIPTION OF THE FIGURES

Numerous aspects and advantages of the present invention will become apparent upon review of the figures, wherein:

FIG. 4 shows the histological evaluation of disease severity in knee joints of rats immunized with bovine type II collagen, after intra-articular injection of either hyaluronic acid alone or an IL-1ra/hyaluronic acid mixture.

FIG. 5 depicts a nucleic acid sequence (SEQ ID NO:1) encoding recombinant human IL-1ra (rhuIL-1ra). Also depicted is the amino acid sequence (SEQ ID NO:2) of rhuIL-1ra, with the initial amino acid being $M_n$ wherein n equal 0 or 1.

DETAILED DESCRIPTION

Figure 1:
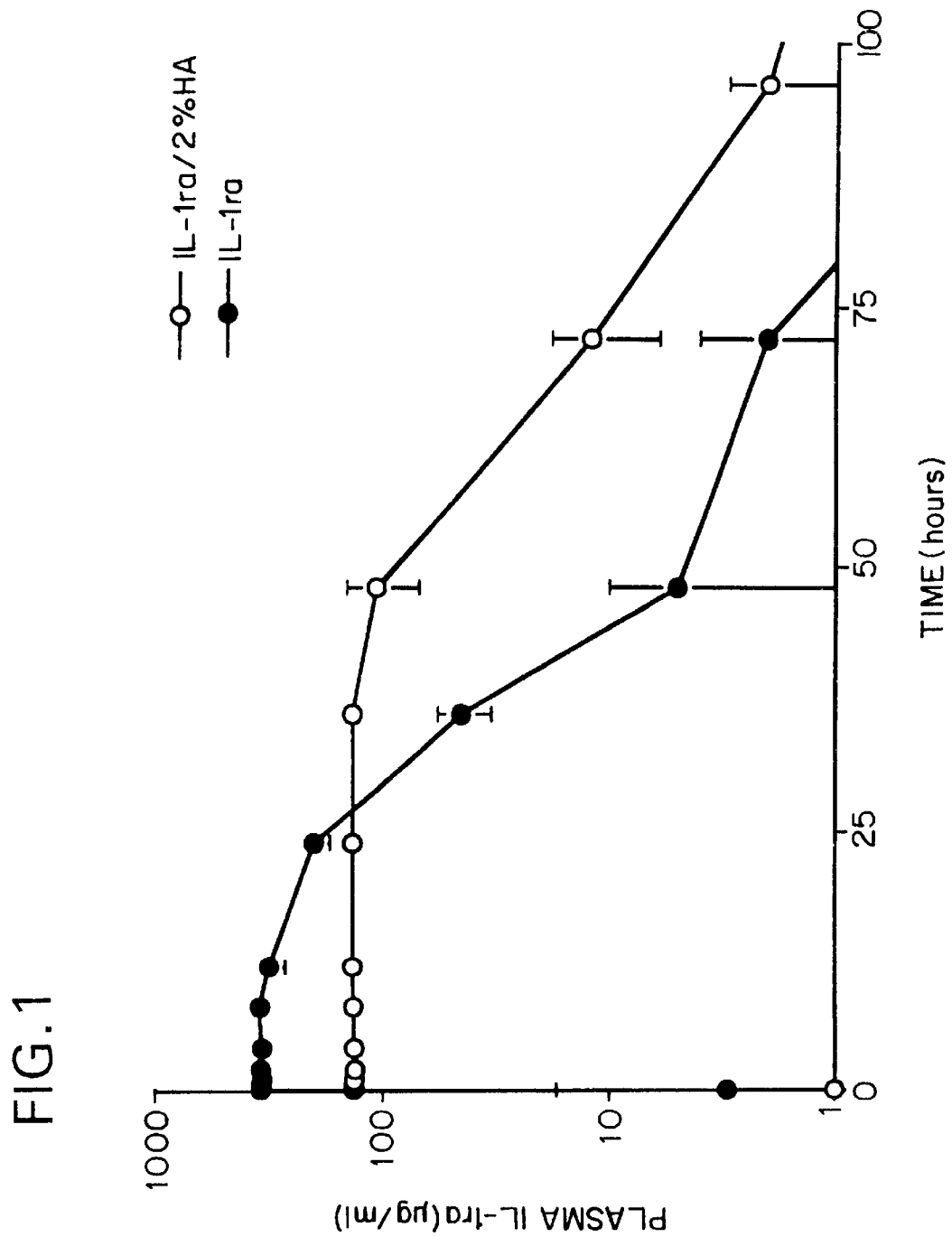
FIG. 1 shows the serum levels of IL-1ra after subcutaneous injection of either IL-1ra alone or IL-1ra mixed with hyaluronic acid.

Pharmaceutical compositions of the present invention contain a mixture of controlled release polymer (e.g., hyaluronan) and a proteinaceous IL-1 inhibitor (e.g., IL-1ra). In a specific embodiment, the present invention is directed to administering a pharmaceutical formulation containing hyaluronan and a proteinaceous IL-1 inhibitor (e.g., IL-1ra), leading to relatively prolonged elevation of IL-1ra levels. The teachings of U.S. Provisional patent application Ser. No. 60/011,419 filed on Feb. 9, 1996 by Collins, entitled on the Provisional Application transmittal letter as "COMPOSITION AND METHOD FOR TREATING INFLAMMATORY DISEASES" (Attorney Docket No. A-365P), U.S. Provisional patent application Ser. No. 60/032,789 filed on Dec. 6, 1996 by Collins and Bevilacqua, entitled on the Provisional Application transmittal letter as "COMPOSITION AND METHOD FOR TREATING INFLAMMATORY DISEASES" (Attorney Docket No. A-365A-P) and U.S. Provisional patent application Ser. No. 60/036,241 filed on Jan. 23, 1997 by Collins and Bevilacqua, entitled on the Provisional Application transmittal letter as "COMPOSITION AND METHOD FOR TREATING INFLAMMATORY DISEASES" (Attorney Docket No. A-365B-P), the disclosures of which are hereby incorporated by reference.

The controlled release polymer may be selected from bulk erosion polymers (e.g., poly(lactic-co-glycolic acid) (PLGA) copolymers, PLGA polymer blends, block copolymers of PEG, and lactic and glycolic acid, poly (cyanoacrylates)); surface erosion polymers (e.g., poly (anhydrides) and poly(ortho esters)); hydrogel esters (e.g., pluronic polyols, poly(vinyl alcohol), poly (vinylpyrrolidone), maleic anhydride-alkyl vinyl ether copolymers, cellulose, hyaluronan, alginate, collagen, gelatin, albumin, and starches and dextrans) and composition systems thereof; or preparations of liposomes or microspheres. Such compositions may influence the physical state, stability, rate of in vivo release, and rate of in vivo clearance of the present proteins and derivatives. The optimal pharmaceutical formulation for a desired protein will be determined by one skilled in the art depending upon the route of administration and desired dosage. Exemplary pharmaceutical compositions are disclosed in Gombotz and Pettit (1995), *Bioconjugate Chem.*, 6:332–351 and *Remington's Pharmaceutical Sciences*, 18th Ed. (1990), Mack Publishing Co., Easton, Pa. 18042, pages 1435–1712, the disclosures of which are hereby incorporated by reference. Specific sustained release compositions are available from the following suppliers: Depotech (Depofoam™, a multivesicular liposome) and Alkermes (ProLease™, a PLGA microsphere).

In a specific embodiment, the present invention is directed to drug delivery systems based on hyaluronan in soluble or non-soluble cross-linked forms. As used herein, hyaluronan is intended to include hyaluronan, hyaluronic acid, salts thereof (such as sodium hyaluronate), esters, ethers, enzymatic derivatives and cross-linked gels of hyaluronic acid, and chemically modified derivatives of hyaluronic acid (such as hylan). Non-modified or modified hyaluronic acid serves as a vehicle which provides slow release of a drug from a system.

The hyaluronan may be of any type already recognized as useful for such purposes. It may be extracted from various non-limiting materials such as rooster combs or umbilical cords or from bacterial cultures such as those of hemolytic group A or C streptococci. It should be pure enough to avoid provoking an adverse or toxic reaction in the mammal being treated. This implies that it be free of pyrogens and have a sufficiently low level of proteins and/or nucleic acids with which hyaluronan is naturally associated, so that no substantial immune reaction is provoked. Suitable purification procedures are described in U.S. Pat. No. 4,141,973, U.S. Pat. No. 5,411,874, U.S. Pat. No. 5,442,053, U.S. Pat. No. 5,559,104, U.S. Pat. No. 5,563,051 and Japanese Patent Application Nos. 14594/1977, 67100/1979 and 74796/1980, the disclosures of which are hereby incorporated by reference.

The hyaluronan may be in its free acid form or in any pharmacologically acceptable salt form. Also, as salts, there may be mentioned an alkali metal salt such as sodium or potassium salt and an alkaline earth metal salt such as calcium or magnesium salt. The preferred source of hyaluronan is a culture of an appropriate microorganism.

Hyaluronan having a molecular weight within a wide range can be used in the present invention. The molecular weight of hyaluronan is generally between $0.1 \times 10^6$ and $1 \times 10^7$, preferably between $0.5 \times 10^6$ and $1 \times 10^7$, more preferably between $2 \times 10^6$ and $1 \times 10^7$ and most preferably between $4 \times 10^6$ and $5 \times 10^6$.

Increasing the molecular weight of hyaluronan by crosslinking has been accomplished in a number of ways. Sakuria et al. in U.S. Pat. No. 4,716,224, disclose crosslinked hyaluronic acid or salts thereof prepared by crosslinking hyaluronic acid or its salts with a polyfunctional epoxide. In U.S. Pat. No. 4,863,907, Sakuri et al. disclose crosslinked glycosaminoglycan or salts thereof prepared by crosslinking a glycosaminoglycan or a salt thereof with a polyfunctional epoxy compound. Huang et al., in European Patent Application No. 0 507 604 A2, disclose ionically crosslinked carboxyl-containing polysaccharides where the crosslinking agent is a compound possessing a trivalent cation. Malson et al., in U.S. Pat. No. 4,716,154 and U.S. Pat. No. 4,772,419 disclose crosslinking hyaluronic acid with bi- or polyfunctional epoxides or their corresponding halohydrins, epihalohydrins or halides, and divinyl sulfone. In. U.S. Pat. No. 4,957,744, della Valle et al. disclose crosslinking esters of hyaluronic acid prepared by esterifying the carboxyl groups of hyaluronic acid with polyhydric alcohols. Balazs et al., in U.S. Pat. Nos. 4,582,865, 4,605, 691 and 4,636,524, disclose crosslinking of hyaluronic acid and its salts, and of other polysaccharides, by reaction with divinyl sulfone. In U.S. Pat. Nos. 5,128,326 and 4,582,865, Balazs et al. disclose crosslinking hyaluronic acid with formaldehyde, epoxides, polyaziridyl compounds and divinyl sulfone. In U.S. Pat. No. 4,713,448, Balazs et al. disclose chemically modifying hyaluronic acid by reaction with aldehydes such as formaldehyde, glutaraldehyde and glyoxal and teach the possibility that crosslinking has occurred. In U.S. Pat. No. 5,356,883, Kuo et al. disclose crosslinking hyaluronic acid by reaction with biscarbodiimides. In EP 0 718 312 A2, Nguyen discloses crosslinking hyaluronic acid or its salts, and of other polysaccharides, by reaction with di- or polyanhydrides.

The hyaluronan concentration in the products, based on the soluble polymers, can be in the range of from about 0.05% to 5% by wt. and higher, depending on the end use of the product, preferably between 0.1% to 4% by wt, more preferably between 1% to 3% by weight. The concentration of IL-1 inhibitor can be varied over very broad limits and preferably should be chosen depending upon the solubility of the IL-1 inhibitor, its pharmacological activity, the desirable effect of the end product, etc.

The crosslinked hyaluronan is usually dissolved in a solvent (e.g., physiological saline) to such a sufficient viscosity to pass through an injection needle. Low viscosity material greatly facilitates the injection by allowing, for instance, the use of a concentrated aqueous hyaluronan solution in practical size doses. Thus, for example, a 1% aqueous solution of hyaluronan can be readily utilized for injection doses of about 10 milliliters, which each contain about 100 milligrams of active ingredient if its viscosity is less than about 200 c/s at 37° C. (as determined using a Cannon-Manning Semi-Micro Viscometer according to the procedures in ASTM D 445 and D 2515).

The drug delivery system according to the present invention includes the following:

1) hyaluronan solutions in which a drug substance is dissolved or dispersed;
2) a cross-linked hyaluronan gel forming a macromolecular "cage" in which a drug substance is dispersed;
3) A cross-linked mixed gel of hyaluronan and at least one other hydrophilic polymer in which a drug substance is dispersed; and
4) A cross-linked gel of hyaluronan or cross-linked mixed gel of hyaluronan and at least one other hydrophilic polymer containing a drug substance which is covalently attached to the macromolecules of hyaluronic acid or the other polymer.

There are several methods for combining a drug with the gel and, accordingly, several types of products which can be obtained.

One of the methods comprises diffusing a drug into a gel when the gel is put into a solution of the drug. The diffusion process is usually slow and depends upon the drug concentration, temperature of the solution, size of the gel particles, etc. The product obtained by this method is a gel in which a drug substance is uniformly dispersed.

The same type of product can be obtained by dehydrating a hyaluronan gel and reswelling it in a drug solution. To dehydrate a gel one can use a water-miscible organic solvent or, alternatively, water from a gel can be removed by drying. However, it is preferable to use a solvent because after drying at a low or elevated temperature, the gel cannot re-swell to its initial degree of swelling. On the other hand, after dehydrating with a solvent, the gel swells to the same volume it had before the treatment. Preferable solvents are ethanol and isopropanol, and ketones such as acetone, though other solvents can also be used.

Yet another method can be used to obtain products of this type. This method comprises allowing a concentrated hyaluronic acid gel resulting from a cross-linking reaction previously carried out in a relatively concentrated solution of hyaluronan to swell in a solution of a drug substance.

Although these three methods all result in products which are essentially the same, each of the methods has certain advantages when compared to any of the other methods for any specific product and, hence, the choice of method should be made with consideration given to such parameters as nature of the drug, the desired concentration of the drug in the system, the delivery rate, etc.

In order to obtain a hyaluronan solution in which a drug substance is dissolved or dispersed, any conventional method can be used. Hyaluronan from any source can be dissolved in water or in physiological saline to a desired concentration and then a drug is dissolved or dispersed in the resulting solution. Alternatively, a solution or dispersion of a drug can be mixed with hyaluronan solution. The polymer concentration is chosen depending upon the end use of the product and the molecular weight of hyaluronan. It is preferable to use a high molecular weight polymer, i.e., a hyaluronan with a molecular weight of $1\times10^6$ or higher. The usable concentration of hyaluronan of this molecular weight can vary from as low as 0.1 wt. percent to as high as 2 wt. percent and even higher for injectable formulations. The drug concentration is chosen depending upon the desired activity of the product.

To load a cross-linked swollen gel with a drug using the diffusion process, the gel can be put into a drug solution. The time for completion of this process depends upon gel particle size, gel swelling ratio, temperature of the process, stirring, concentration of the drug in the solution, etc. By proper combination of these parameters, a swollen gel can be loaded with a drug in a relatively short period of time.

To dehydrate a cross-linked gel with a solvent, it is enough to put the gel in any form (i.e., as fine particles or as a membrane) into a solvent, preferably a volatile solvent (e.g., isopropanol), and keep it in the solvent for a sufficient amount of time to remove water from the gel. The degree of water removal depends upon the size of the particles or the membrane thickness, the gel/solvent ratio, etc. Treatment with a solvent can be repeated several times, if desired. The solvent from the gel can be removed by drying under normal pressure or in a vacuum at room or elevated temperature. The thusly dehydrated gel, when put into a drug solution, reswells to the initial swelling ratio.

Exemplary forms of hyaluronan are disclosed in Peyron and Balazs (1974), *Path. Biol.,* 22(8):731–736; Isdale et al. (1991), *J. Drug Dev.,* 4(2):93–99; Larsen et al. (1993), *Journal of Biomedical Materials Research,* 27:1129–1134; Namiki, et al. (1982), *International Journal of Clinical Pharmacology, Therapy and Toxicology,* 20(11):501–507; Meyer et al. (1995), Journal of Controlled Release, 35:67–72; Kikuchi et al. (1996), *Osteoarthritis and Cartilage,* 4:99–110; Sakakibara et al. (1994), *Clinical Orthopaedics and Related Research,* 299:282–292; Meyers and Brandt (1995), 22(9):1732–1739; Laurent et al. (1995), *Acta Orthop Scand,* 66(266):116–120; Cascone et al. (1995), *Biomaterials,* 16(7):569–574; Yerashalmi et al. (1994), *Archives of Biochemistry and Biophysics,* 313(2):267–273; Bernatchez et al. (1993), *Journal of Biomedical Materials Research,* 27(5):677–681; Tan et al. (1990), *Australian Journal of Biotechnology,* 4(1):38–43; Gombotz and Pettit (1995), *Bioconjugate Chem.,* 6:332–351; U.S. Pat. Nos. 4,582,865, 4,605,691, 4,636,524, 4,713,448, 4,716,154, 4,716,224, 4,772,419, 4,851,521, 4,957,774, 4,863,907, 5,128,326, 5,202,431, 5,336,767, 5,356,883; European Patent Application Nos. 0 507 604 A2 and 0 718 312 A2; and WO 96/05845, the disclosures of which are hereby incorporated by reference. Specific hyaluronan compositions are available from the following suppliers: BioMatrix, Inc. Ridgefield, N.J. (Synvisc™, a 90:10 mixture of a hylan fluid and hylan gel); Fidia S.p.A., Abano Terme, Italy (Hyalgan™, the sodium salt of a rooster comb-derived hyaluronic acid (~500,000 to ~700,000 MW)); Kaken Pharmaceutical Co., Ltd., Tokyo, Japan (Artz™, a 1% solution of a rooster-comb derived hyaluronic acid, ~700,000 MW); Pharmacia AB, Stockholm, Sweden (Healon™, a rooster-comb derived hyaluronic acid, ~$4\times10^6$ MW); Genzyme Corporation, Cambridge, Mass. (Surgicoat™, a recombinant hyaluronic acid); Pronova Biopolymer, Inc. Portsmouth, N.H. (Hyaluronic Acid FCH, a high molecular weight (e.g., ~$1.5$–$2.2\times10^6$ MW) hyaluronic acid prepared from cultures of *Streptococcus zooepidemicus;* Sodium Hyaluronate MV, ~$1.0$–$1.6\times10^6$ MW and Sodium Hyaluronate LV, ~$1.5$–$2.2\times10^6$ MW); Calbiochem-Novabiochem AB, Lautelfingen, Switzerland (Hyaluronic Acid, sodium salt (1997 company catalog number 385908) prepared from Streptococcus sp.); Intergen Company, Purchase, N.Y. (a rooster-comb derived hyaluronic acid, >$1\times10^6$ MW); Diosynth Inc., Chicago, Ill.; Amerchol Corp., Edison, N.J. and Kyowa Hakko Kogyo Co., Ltd., Tokyo, Japan.

Interleukin-1 inhibitors may be from any protein capable of specifically preventing activation of cellular receptors to IL-1. Classes of interleukin-1 inhibitors include: interleukin-1 receptor antagonists such as IL-1ra, as described below; anti-IL-1 receptor monoclonal antibodies (EP 623674); IL-1 binding proteins such as soluble IL-1 receptors (U.S. Pat. Nos. 5,492,888, 5,488,032, 5,464,937, 5,319,071 and 5,180,812); anti-IL-1 monoclonal antibodies, (WO 9501997, WO 9402627, WO 9006371, U.S. Pat. No. 4,935,343, EP 364778, EP 267611 and EP 220063); and IL-1 receptor accessory proteins, (WO 96/23067), the disclosures of which are incorporated herein by reference.

Preferred IL-1ra, as well as methods of making and using thereof, are described in U.S. Pat. No. 5,075,222 (referred to herein as the '222 patent); WO 91/08285; WO 91/17184; AU 9173636; WO 92/16221 and WO 96/22793, the disclosures of which are incorporated herein by reference. The proteins include glycosylated as well as non-glycosylated IL-1 receptor antagonists.

Specifically, three useful forms of IL-1ra and variants thereof are disclosed and described in the '222 patent. The first of these, IL-1raα, is characterized as a 22–23 kD molecule on SDS-PAGE with an approximate isoelectric point of 4.8, eluting from a Mono Q FPLC column at around 52 mM NaCl in Tris buffer, pH 7.6. The second, IL-1raβ, is characterized as a 22–23 kD protein, eluting from a Mono Q column at 48 mM NaCl. Both IL-1raα and IL-1raβ are glycosylated. The third, IL-1rax, is characterized as a 20 kD protein, eluting from a Mono Q column at 48 mM NaCl, and is non-glycosylated. All three of these inhibitors possess similar functional and immunological activities.

Methods for producing IL-1ra are also disclosed in the '222 patent. One disclosed method consists of isolating the IL-1ra from human monocytes, where they are naturally produced. A second disclosed method involves isolating the gene responsible for coding IL-1ra, cloning the gene in suitable vectors and cells types, expressing the gene to produce the inhibitors and harvesting the inhibitors. The latter method, which is exemplary of recombinant DNA methods in general, is a preferred method. Recombinant DNA methods are preferred in part because they are capable of achieving comparatively greater amounts of protein at greater purity. Thus, the invention also encompasses IL-1ra containing an N-terminal methionyl group as a consequence of expression in prokaryotic cells, such as E. coli.

As stated above, the present invention also includes modified forms of IL-1ra. The modified forms of IL-1ra as used herein include variant polypeptides in which amino acids have been (1) deleted from ("deletion variants"), (2) inserted into ("addition variants") or (3) substituted for ("substitution variants") residues within the amino acid sequence of IL-1ra.

For IL-1ra deletion variants, each polypeptide may typically have an amino sequence deletion ranging from about 1 to 30 residues, more typically from about 1 to 10 residues and most typically from about 1 to 5 contiguous residues. N-terminal, C-terminal and internal intrasequence deletions are contemplated. Deletions within the IL-1ra amino acid sequence may be made in regions of low homology with the sequences of other members of the IL-1 family. Deletions within the IL-1ra amino acid sequence may be made in areas of substantial homology with the sequences of other members of the IL-1 family and will be more likely to significantly modify the biological activity.

For IL-1ra addition variants, each polypeptide may include an amino- and/or carboxyl-terminal fusion ranging in length from one residue to one hundred or more residues, as well as internal intrasequence insertions of single or multiple amino acid residues. Internal additions may range typically from about 1 to 10 amino acid residues, more typically from about 1 to 5 amino acid residues and most typically from about 1 to 3 amino acid residues.

Amino-terminus addition variants include the addition of a methionine (for example, as an artifact of the direct expression of the protein in bacterial recombinant cell culture) or an additional amino acid residue or sequence. A further example of an amino-terminal insertion includes the fusion of a signal sequence, as well as or with other pre-pro sequences, to facilitate the secretion of protein from recombinant host cells. Each polypeptide may comprise a signal sequence selected to be recognized and processed, i.e., cleaved by a signal peptidase, by the host cell. For prokaryotic host cells that do not recognize and process the native IL-1ra signal sequence, each polypeptide may comprise a prokaryotic signal sequence selected, for example, from the group of the alkaline phosphatase, penicillinase or heat-stable enterotoxin II leaders. For yeast cells, each polypeptide may have a signal sequence selected, for example, from the group of the yeast invertase, alpha factor or acid phosphatase leader sequences. For mammalian cell expression, each polypeptide may have the native signal sequence of IL-1ra, although other mammalian signal sequences may be suitable, for example, sequences derived from other IL-1 family members.

Carboxy-terminus addition variants include chimeric proteins wherein each comprises the fusion of IL-1ra with all or part of a constant domain of a heavy or light chain of human immunoglobulin. Such chimeric proteins are preferred wherein the immunoglobulin portion of each comprises all domains except the first domain of the constant region of the heavy chain of human immunoglobulin, such as IgG, IgA, IgM or IgE (especially IgG, e.g., IgG1 or IgG3). A skilled artisan will appreciate that any amino acid of each immunoglobulin portion can be deleted or substituted with one or more amino acids, or one or more amino acids can be added as long as the IL-1ra still antagonizes the IL-1 receptor, and the immunoglobulin portion shows one or more of its characteristic properties.

For IL-1ra substitution variants, each such polypeptide may have at least one amino acid residue in IL-1ra removed and a different residue inserted in its place. Substitution variants include allelic variants, which are characterized by naturally-occurring nucleotide sequence changes in the species population that may or may not result in an amino acid change. One skilled in the art can use any information known about the binding or active site of the polypeptide in the selection of possible mutation sites. Exemplary substitution variants are taught in WO 91/17184, WO 92/16221, and WO 96/09323.

One method for identifying amino acid residues or regions for mutagenesis of a protein is called "alanine scanning mutagenesis" (Cunningham and Wells (1989), Science, 244:1081–1085, the disclosure of which is hereby incorporated by reference). In this method, an amino acid residue or group of target residues of a protein is identified (e.g., charged residues such as Arg, Asp, His, Lys and Glu) and replaced by a neutral or negatively-charged amino acid (most preferably alanine or polyalanine) to effect the interaction of the amino acids with the surrounding aqueous environment in or outside the cell. Those residues demonstrating functional sensitivity to the substitutions are then refined by introducing additional or alternate residues at the sites of substitution. Thus, the site for introducing an amino acid sequence modification is predetermined and, to optimize the performance of a mutation at a given site, alanine scanning or random mutagenesis may be conducted and the resulting variant polypeptide is screened for the optimal combination of desired activity and degree of activity.

The sites of greatest interest for substitutional mutagenesis include sites where the amino acids found in IL-ra are substantially different in terms of side-chain bulk, charge and/or hydrophobicity from IL-1ra-like proteins such as IL-1ra's of other various species or of other members of the IL-1 family. Other sites of interest include those in which particular residues of IL-1ra are identical with those of such IL-1ra-like proteins. Such positions are generally important for the biological activity of a protein. Initially, these sites are modified by substitution in a relatively conservative manner. Such conservative substitutions are shown in Table 1 under the heading of "Preferred Substitutions". If such substitutions result in a change in biological activity, then more substantial changes (Exemplary Substitutions) are introduced and/or other additions/deletions may be made and the resulting polypeptides screened.

TABLE 1

Amino Acid Substitutions

| Original Residue | Preferred Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Lys; Arg |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Arg | Asn; Gln; Lys; Arg |
| Ile (I) | Leu | Leu; Val; Met; Ala; Phe; norleucine |
| Leu (L) | Ile | norleucine; Ile; Val; Met; Ala; Phe |
| Lys (K) | Arg | Arg; Gln; Asn |
| Met (M) | Leu | Leu; Phe; Ile |
| Phe (F) | Leu | Leu; Val; Ile; Ala |
| Pro (P) | Gly | Gly |
| Ser (S) | Thr | Thr |
| Thr (T) | Ser | Ser |
| Trp (W) | Tyr | Tyr |
| Tyr (Y) | Phe | Trp; Phe; Thr; Ser |
| Val (V) | Leu | Ile; Leu; Met; Phe; Ala; norleucine |

Conservative modifications to the amino acid sequence (and the corresponding modifications to the encoding nucleic acid sequence) of IL-1ra are expected to produce proteins having similar functional and chemical characteristics. In contrast, substantial modifications in the functional and/or chemical characteristics of IL-1ra may be accomplished by selecting substitutions that differ significantly in their effect on maintaining (a) the structure of the polypeptide backbone in the area of the substitution, for example, as a sheet or helical conformation, (b) the charge or hydrophobicity of the protein at the target site or (c) the bulk of the side chain. Naturally-occurring residues are divided into groups based on common side chain properties:

1) hydrophobic: norleucine, Met, Ala, Val, Leu, Ile;
2) neutral hydrophilic: Cys, Ser, Thr;
3) acidic: Asp, Glu;
4) basic: Asn, Gln, His, Lys, Arg;
5) aromatic: Trp, Tyr, Phe; and
6) residues that influence chain orientation: Gly, Pro.

Non-conservative substitutions may involve the exchange of a member of one of these groups for another. Such substituted residues may be introduced into regions of IL-1ra that are homologous or non-homologous with other IL-1 family members.

Specific mutations in the sequence of IL-1ra may involve substitution of a non-native amino acid at the N-terminus, C-terminus or at any site of the protein that is modified by the addition of an N-linked or O-linked carbohydrate. Such modifications may be of particular utility, such as in the addition of an amino acid (e.g., cysteine), which is advantageous for the linking of a water soluble polymer to form a derivative, as described below. Further, the sequence of IL-1ra may be modified to add glycosylation sites or to delete N-linked or O-linked glycosylation sites. An asparagine-linked glycosylation recognition site comprises a tripeptide sequence which is specifically recognized by appropriate cellular glycosylation enzymes. These tripeptide sequences are either Asn-Xaa-Thr or Asn-Xaa-Ser, where Xaa can be any amino acid other than Pro.

In a specific embodiment, the variants are substantially homologous to the amino acid of IL-1ra (SEQ ID NO:2). The term "substantially homologous" as used herein means a degree of homology that is preferably in excess of 70%, more preferably in excess of 80%, even more preferably in excess of 90% or most preferably even 95%. The percentage of homology as described herein is calculated as the percentage of amino acid residues found in the smaller of the two sequences which align with identical amino acid residues in the sequence being compared when four gaps in a length of 100 amino acids may be introduced to assist in that alignment, as set forth by Dayhoff in *Atlas of Protein Sequence and Structure,* 5:124 (1972), National Biochemical Research Foundation, Washington, D.C., the disclosure of which is hereby incorporated by reference. Also included as substantially homologous are variants of IL-1ra which may be isolated by virtue of cross-reactivity with antibodies to the amino acid sequence of SEQ ID NO:2 or whose genes may be isolated through hybridization with the DNA of SEQ ID NO:1 or with segments thereof.

The production of variants of IL-1ra is described in further detail below. Such variants may be prepared by introducing appropriate nucleotide changes into the DNA encoding variants of IL-1ra or by in vitro chemical synthesis of the desired variants of IL-1ra. It will be appreciated by those skilled in the art that many combinations of deletions, insertions and substitutions can be made, provided that the final variants of IL-1ra are biologically active.

Mutagenesis techniques for the replacement, insertion or deletion of one or more selected amino acid residues are well known to one skilled in the art (e.g., U.S. Pat. No. 4,518,584, the disclosure of which is hereby incorporated by reference). There are two principal variables in the construction of each amino acid sequence variant, the location of the mutation site and the nature of the mutation. In designing each variant, the location of each mutation site and the nature of each mutation will depend on the biochemical characteristic(s) to be modified. Each mutation site can be modified individually or in series, e.g., by (1) substituting first with conservative amino acid choices and then with more radical selections, depending upon the results achieved, (2) deleting the target amino acid residue or (3) inserting one or more amino acid residues adjacent to the located site.

Chemically modified derivatives of IL-1ra and variants of IL-1ra may be prepared by one skilled in the art, given the disclosures herein. Conjugates may be prepared using glycosylated, non-glycosylated or de-glycosylated IL-1ra and variants of IL-1ra. Typically, non-glycosylated IL-1ra and variants of IL-1ra will be used. Suitable chemical moieties for derivatization of IL-1ra and variants of IL-1ra include water soluble polymers.

Water soluble polymers are desirable because the protein to which each is attached will not precipitate in an aqueous environment, such as a physiological environment. Preferably, the polymer will be pharmaceutically acceptable for the preparation of a therapeutic product or composition. One skilled in the art will be able to select the desired polymer based on such considerations as whether the polymer/protein conjugate will be used therapeutically and, if so, the desired dosage, circulation time and resistance to proteolysis.

Suitable, clinically acceptable, water soluble polymers include but are not limited to polyethylene glycol (PEG), polyethylene glycol propionaldehyde, copolymers of ethylene glycol/propylene glycol, monomethoxy-polyethylene glycol, carboxymethylcellulose, dextran, polyvinyl alcohol (PVA), polyvinyl pyrrolidone, poly-1, 3-dioxolane, poly-1, 3,6-trioxane, ethylene/maleic anhydride copolymer, poly ($\beta$-amino acids) (either homopolymers or random copolymers), poly(n-vinyl pyrrolidone)polyethylene glycol, propropylene glycol homopolymers (PPG) and other polyakylene oxides, prolypropylene oxide/ethylene oxide copolymers, polyoxyethylated polyols (POG) (e.g., glycerol) and other polyoxyethylated polyols, polyoxyethylated sorbitol, or polyoxyethylated glucose, colonic acids or other carbohydrate polymers, Ficoll or dextran and mixtures thereof.

As used herein, polyethylene glycol is meant to encompass any of the forms that have been used to derivatize other proteins, such as mono-(C1–C10) alkoxy- or aryloxy-polyethylene glycol. Polyethylene glycol propionaldehyde may have advantages in manufacturing due to its stability in water.

The water soluble polymers each may be of any molecular weight and may be branched or unbranched. The water soluble polymers each typically have an average molecular weight of between about 2 kDa to about 100 kDa (the term "about" indicating that in preparations of a water soluble polymer, some molecules will weigh more, some less, than the stated molecular weight). The average molecular weight of each water soluble polymer preferably is between about 5 kDa and about 50 kDa, more preferably between about 12 kDa and about 25 kDa and most preferably about 20 kDa. Generally, the higher the molecular weight or the more branches, the higher the polymer:protein ratio. Other sizes may be used, depending on the desired therapeutic profile (e.g., the duration of sustained release; the effects, if any, on biological activity; the ease in handling; the degree or lack of antigenicity and other known effects of a water soluble polymer on a therapeutic protein).

The water soluble polymers each should be attached to the protein with consideration of effects on functional or antigenic domains of the protein. In general, chemical derivatization may be performed under any suitable condition used to react a protein with an activated polymer molecule. Activating groups which can be used to link the polymer to the active moieties include the following: sulfone, maleimide, sulfhydryl, thiol, triflate, tresylate, azidirine, oxirane and 5-pyridyl.

The water soluble polymers each are generally attached to the protein at the $\alpha$- or $\epsilon$-amino groups of amino acids or a reactive thiol group, but it is also contemplated that a water soluble group could be attached to any reactive group of the protein which is sufficiently reactive to become attached to a water soluble group under suitable reaction conditions. Thus, a water soluble polymer may be covalently bound to a protein via a reactive group, such as a free amino or carboxyl group. The amino acid residues having a free amino group may include lysine residues and the N-terminal amino acid residue. Those having a free carboxyl group may include aspartic acid residues, glutamic acid residues and the C-terminal amino acid residue. Those having a reactive thiol group include cysteine residues.

Methods for preparing proteins conjugated with water soluble polymers will each generally comprise the steps of (a) reacting a protein with a water soluble polymer under conditions whereby the protein becomes attached to one or more water soluble polymers and (b) obtaining the reaction product. Reaction conditions for each conjugation may be selected from any of those known in the art or those subsequently developed, but should be selected to avoid or limit exposure to reaction conditions such as temperatures, solvents and pH levels that would inactivate the protein to be modified. In general, the optimal reaction conditions for the reactions will be determined case-by-case based on known parameters and the desired result. For example, the larger the ratio of water soluble polymer:protein conjugate, the greater the percentage of conjugated product. The optimum ratio (in terms of efficiency of reaction in that there is no excess unreacted protein or polymer) may be determined by factors such as the desired degree of derivatization (e.g., mono-, di-, tri-, etc.), the molecular weight of the polymer selected, whether the polymer is branched or unbranched and the reaction conditions used. The ratio of water soluble polymer (e.g., PEG) to protein will generally range from 1:1 to 100:1. One or more purified conjugates may be prepared from each mixture by standard purification techniques, including among others, dialysis, salting-out, ultrafiltration, ion-exchange chromatography, gel filtration chromatography and electrophoresis.

One may specifically desire an N-terminal chemically modified protein. One may select a water soluble polymer by molecular weight, branching, etc., the proportion of water soluble polymers to protein (or peptide) molecules in the reaction mix, the type of reaction to be performed, and the method of obtaining the selected N-terminal chemically modified protein. The method of obtaining the N-terminal chemically modified protein preparation (i.e., separating this moiety from other monoderivatized moieties if necessary) may be by purification of the N-terminal chemically modified protein material from a population of chemically modified protein molecules. Selective N-terminal chemical modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved. For example, one may selectively attach a water soluble polymer to the N-terminus of the protein by performing the reaction at a pH which allows one to take advantage of the pKa differences between the $\epsilon$-amino group of the lysine residues and that of the $\alpha$-amino group of the N-terminal residue of the protein. By such selective derivatization, attachment of a water soluble polymer to a protein is controlled: the conjugation with the polymer takes place predominantly at the N-terminus of the protein and no significant modification of other reactive groups, such as the lysine side chain amino groups, occurs.

Using reductive alkylation, the water soluble polymer may be of the type described above, and should have a single reactive aldehyde for coupling to the protein. Polyethylene glycol propionaldehyde, containing a single reactive aldehyde, may be used.

The present invention specifically contemplates the chemically derivatized protein to include mono- or poly- (e.g., 2–4) PEG moieties. Pegylation may be carried out by any of the pegylation reactions known in the art. Methods for preparing a pegylated protein product will generally comprise the steps of (a) reacting a protein product with polyethylene glycol (such as a reactive ester or aldehyde derivative of PEG) under conditions whereby the protein becomes attached to one or more PEG groups and (b) obtaining the reaction product(s). In general, the optimal reaction conditions for the reactions will be determined case-by-case based on known parameters and the desired result.

There are a number of attachment methods available to those skilled in the art. See, for example, EP 0 401 384, the disclosure of which is hereby incorporated by reference; see also, Malik et al. (1992), *Exp. Hematol.*, 20:1028–1035; Francis (1992), *Focus on Growth Factors*, 3(2):4–10, (published by Mediscript, Mountain Court, Friern Barnet Lane, London N20 OLD, UK); EP 0 154 316; EP 0 401 384; WO 92/16221; WO 95/34326; and the other publications cited herein that relate to pegylation, the disclosures of which are hereby incorporated by reference.

The pegylation specifically may be carried out via an acylation reaction or an alkylation reaction with a reactive polyethylene glycol molecule. Thus, protein products according to the present invention include pegylated proteins wherein the PEG group(s) is (are) attached via acyl or alkyl groups. Such products may be mono-pegylated or poly-pegylated (e.g., containing 2–6, and preferably 2–5, PEG groups). The PEG groups are generally attached to the protein at the α- or ε-amino groups of amino acids, but it is also contemplated that the PEG groups could be attached to any amino group attached to the protein which is sufficiently reactive to become attached to a PEG group under suitable reaction conditions.

Pegylation by acylation generally involves reacting an active ester derivative of polyethylene glycol (PEG) with the protein. For the acylation reactions, the polymer(s) selected should have a single reactive ester group. Any known or subsequently discovered reactive PEG molecule may be used to carry out the pegylation reaction. A preferred activated PEG ester is PEG esterified to N-hydroxysuccinimide (NHS). As used herein, "acylation" is contemplated to include, without limitation, the following types of linkages between the therapeutic protein and a water soluble polymer such as PEG: amide, carbamate, urethane, and the like (see Chamow (1994), *Bioconjugate Chem.*, 5(2):133–140). Reaction conditions may be selected from any of those known in the pegylation art or those subsequently developed, but should avoid conditions such as temperature, solvent and pH that would inactivate the protein to be modified.

Pegylation by acylation will generally result in a poly-pegylated protein. Preferably, the connecting linkage will be an amide. Also preferably, the resulting product will be substantially only (e.g., >95%) mono, di- or tri-pegylated. However, some species with higher degrees of pegylation may be formed in amounts depending on the specific reaction conditions used. If desired, more purified pegylated species may be separated from the mixture (particularly unreacted species) by standard purification techniques, including among others, dialysis, salting-out, ultrafiltration, ion-exchange chromatography, gel filtration chromatography and electrophoresis.

Pegylation by alkylation generally involves reacting a terminal aldehyde derivative of PEG with the protein in the presence of a reducing agent. For the reductive alkylation reaction, the polymer(s) selected should have a single reactive aldehyde group. An exemplary reactive PEG aldehyde is polyethylene glycol propionaldehyde, which is water stable, or mono C1–C10 alkoxy or aryloxy derivatives thereof (see, U.S. Pat. No. 5,252,714).

Pegylation by alkylation can also result in poly-pegylated protein. In addition, one can manipulate the reaction conditions to substantially favor pegylation only at the α-amino group of the N-terminus of the protein (i.e., a mono-pegylated protein). In either case of monopegylation or polypegylation, the PEG groups are preferably attached to the protein via a —CH$_2$—NH— group. With particular reference to the —CH$_2$— group, this type of linkage is referred to herein as an "alkyl" linkage.

Reductive alkylation to produce a substantially homogeneous population of mono-polymer/protein product will generally comprise the steps of: (a) reacting a protein with a reactive PEG molecule under reductive alkylation conditions, at a pH suitable to permit selective modification of the α-amino group at the amino terminus of said protein and (b) obtaining the reaction product(s). Derivatization via reductive alkylation to produce a monopegylated product exploits pKa differences between the lysine amino groups and the α-amino group at the N-terminus (the pKa being the pH at which 50% of the amino groups are protonated and 50% are not).

The reaction is performed at a pH which allows one to take advantage of the pKa differences between the ε-amino groups of the lysine residues and that of the α-amino group of the N-terminal residue of the protein. In general, if the pH is lower, a larger excess of polymer to protein will be desired (i.e., the less reactive the N-terminal α-amino group, the more polymer is needed to achieve optimal conditions). If the pH is higher, the polymer:protein ratio need not be as large (i.e., more reactive groups are available, so fewer polymer molecules are needed). For purposes of the present invention, the pH will generally fall within the range of 3–9, preferably 3–6. For the reductive alkylation, the reducing agent should be stable in aqueous solution and preferably be able to reduce only the Schiff base formed in the initial process of reductive alkylation. Suitable reducing agents may be selected from sodium borohydride, sodium cyanoborohydride, dimethylamine borane, trimethylamine borane and pyridine borane. A particularly suitable reducing agent is sodium cyanoborohydride. Other reaction parameters, such as solvent, reaction times, temperatures and means of purification of products can be determined case-by-case, based on the published information relating to derivatization of proteins with water soluble polymers.

By such selective derivatization, attachment of a water soluble polymer (that contains a reactive group such as an aldehyde) to a protein is controlled: the conjugation with the polymer takes place predominantly at the N-terminus of the protein and no significant modification of other reactive groups, such as the lysine side chain amino groups, occurs. The preparation will typically be greater than 90% monopolymer/protein conjugate, and more typically greater than 95% monopolymer/protein conjugate, with the remainder of observable molecules being unreacted (i.e., protein lacking the polymer moiety).

The pegylation also may specifically be carried out via water soluble polymers having at least one reactive hydroxy group (e.g. polyethylene glycol) can be reacted with a reagent having a reactive carbonyl, nitrile or sulfone group to convert the hydroxyl group into a reactive Michael acceptor, thereby forming an "activated linker" useful in modifying various proteins to provide improved biologically-active conjugates. "Reactive carbonyl, nitrile or sulfone" means a carbonyl, nitrile or sulfone group to which a two carbon group is bonded having a reactive site for thiol-specific coupling on the second carbon from the carbonyl, nitrile or sulfone group (WO 92/16221).

The activated linkers can be monofunctional, bifunctional, or multifunctional. Useful reagents having a reactive sulfone group that can be used in the methods include, without limitation, chlorosulfone, vinylsulfone and divinylsulfone.

In a specific embodiment, the water soluble polymer is activated with a Michael acceptor. WO 95/13312 describes, inter alia, water soluble sulfone-activated PEGs which are highly selective for coupling with thiol moieties instead of amino moieties on molecules and on surfaces. These PEG derivatives are stable against hydrolysis for extended periods in aqueous environments at pHs of about 11 or less, and can form linkages with molecules to form conjugates which are also hydrolytically stable. The linkage by which the PEGs and the biologically active molecule are coupled includes a sulfone moiety coupled to a thiol moiety and has the structure PEG—$SO_2$—$CH_2$—$CH_2$—S—W, where W represents the biologically active molecule, and wherein the sulfone moiety is vinyl sulfone or an active ethyl sulfone. Two particularly useful homobifunctional derivatives are PEG-bis-chlorosulfone and PEG-bis-vinylsulfone.

U.S. patent application Ser. No. 08/473,809, filed Jun. 7, 1995, the disclosure of which is hereby incorporated by reference, teaches methods of making sulfone-activated linkers by obtaining a compound having a reactive hydroxyl group and converting the hydroxyl group to a reactive Michael acceptor to form an activated linker, with the use of tetrahydrofuran (THF) as the solvent for the conversion. U.S. patent application Ser. No. 08/611,918, filed Mar. 6, 1996, the disclosure of which is hereby incorporated by reference, teaches a process for purifying the activated linkers utilizes hydrophobic interaction chromatography to separate the linkers based on size and end-group functionality.

Polynucleotides

The present invention further provides polynucleotides which encode IL-1ra and variants of IL-1ra. Based upon the present description and using the universal codon table, one of ordinary skill in the art can readily determine all of the nucleic acid sequences which encode the amino acid sequences of IL-1ra and variants of IL-1ra.

Recombinant expression techniques conducted in accordance with the descriptions set forth below may be followed to produce these polynucleotides and to express the encoded proteins. For example, by inserting a nucleic acid sequence which encodes IL-1ra or a variant of IL-1ra into an appropriate vector, one skilled in the art can readily produce large quantities of the desired nucleotide sequence. The sequences can then be used to generate detection probes or amplification primers. Alternatively, a polynucleotide encoding IL-1ra or a variant of IL-1ra can be inserted into an expression vector. By introducing the expression vector into an appropriate host, the desired protein may be produced in large amounts.

As further described herein, there are numerous host/ vector systems available for the propagation of desired nucleic acid sequences and/or the production of the desired proteins. These include but are not limited to plasmid, viral and insertional vectors, and prokaryotic and eukaryotic hosts. One skilled in the art can adapt a host/vector system which is capable of propagating or expressing heterologous DNA to produce or express the sequences of the present invention.

Furthermore, it will be appreciated by those skilled in the art that, in view of the present disclosure, the nucleic acid sequences include degenerate nucleic acid sequences encoding IL-1ra having the sequences set forth in FIG. 5 and those nucleic acid sequences which hybridize (preferably under stringent hybridization conditions) to complements of these nucleic acid sequences [Maniatis et al. (1982), *Molecular Cloning* (A Laboratory Manual), Cold Spring Harbor Laboratory, pages 387 to 389]. Exemplary stringent hybridization conditions are hybridization in 4×SSC at 62–67° C., followed by washing in 0.1×SSC at 62–67° C. for approximately an hour. Alternatively, exemplary stringent hybridization conditions are hybridization in 45–55% formamide, 4×SSC at 40–45° C. Also included are DNA sequences which hybridize to the complement of the nucleic acid sequence set forth in SEQ ID NO:1 under relaxed hybridization conditions and which encode the variants of IL-1ra. Examples of such relaxed stringency hybridization conditions are 4×SSC at 45–55° C. or hybridization with 30–40% formamide at 40–45° C.

Also provided by the present invention are recombinant DNA constructs involving vector DNA together with the DNA sequences encoding the desired proteins. In each such DNA construct, the nucleic acid sequence encoding a desired protein (with or without signal peptides) is in operative association with a suitable expression control or regulatory sequence capable of directing the replication and/or expression of the desired protein in a selected host.

Recombinant Expression

Preparation of Polynucleotides

Nucleic acid sequences encoding IL-1ra or variants of IL-1ra can readily be obtained in a variety of ways including, without limitation, chemical synthesis, cDNA or genomic library screening, expression library screening and/ or PCR amplification of cDNA. These methods and others which are useful for isolating such nucleic acid sequences are set forth in Sambrook et al. (1989), *Molecular Cloning: A Laboratory Manual,* Cold Spring Harbor Laboratory Press, Cold Spring Harbor, N.Y.; by Ausubel et al. (1994), eds, *Current Protocols in Molecular Biology,* Current Protocols Press; and by Berger and Kimmel (1987), *Methods in Enzymology: Guide to Molecular Cloning Techniques,* Vol. 152, Academic Press, Inc., San Diego, Calif., the disclosures of which are hereby incorporated by reference.

Chemical synthesis of nucleic acid sequences can be accomplished using methods well known in the art, such as those set forth by Engels et al. (1989), *Angew. Chem. Intl. Ed.,* 28:716–734 and Wells et al. (1985), *Gene,* 34:315, the disclosures of which are hereby incorporated by reference. These methods include, inter alia, the phosphotriester, phosphoramidite and H-phosphonate methods of nucleic acid sequence synthesis. Large nucleic acid sequences, for example those larger than about 100 nucleotides in length, can be synthesized as several fragments. The fragments can then be ligated together to form nucleic acid sequences encoding a desired protein. A preferred method is polymer-supported synthesis using standard phosphoramidite chemistry.

Alternatively, a suitable nucleic acid sequence may be obtained by screening an appropriate cDNA library (i.e., a library prepared from one or more tissue sources believed to express the protein) or a genomic library (a library prepared from total genomic DNA). The source of the cDNA library is typically a tissue from any species that is believed to express a desired protein in reasonable quantities. The source of the genomic library may be any tissue or tissues from any mammalian or other species believed to harbor a gene encoding a desired protein.

Hybridization mediums can be screened for the presence of DNA encoding a desired protein using one or more nucleic acid probes (oligonucleotides, cDNA or genomic DNA fragments that possess an acceptable level of homology to the cDNA or gene to be cloned) that will hybridize selectively with cDNA(s) or gene(s) present in the library. The probes typically used for such screening encode a small region of DNA sequence from the same or a similar species as the species from which the library was prepared. Alternatively, the probes may be degenerate, as discussed herein.

Hybridization is typically accomplished by annealing an oligonucleotide probe or cDNA to the clones under conditions of stringency that prevent non-specific binding but permit binding of those clones that have a significant level of homology with the probe or primer. Typical hybridization and washing stringency conditions depend in part on the size (e.g., number of nucleotides in length) of the cDNA or oligonucleotide probe and whether the probe is degenerate. The probability of identifying a clone is also considered in designing the hybridization medium (e.g., whether a cDNA or genomic library is being screened).

Where a DNA fragment (such as a cDNA) is used as a probe, typical hybridization conditions include those as set forth in Ausubel et al. (1994), eds., supra. After hybridization, the hybridization medium is washed at a suitable stringency depending on several factors such as probe size, expected homology of probe to clone, the hybridization medium being screened, the number of clones being screened and the like. Examples of stringent washing solutions, which are usually low in ionic strength and are used at relatively high temperatures, are as follows: one such stringent wash is 0.015 M NaCl, 0.005 M NaCitrate and 0.1% SDS at 55–65° C.; another such stringent wash is 1 mM $Na_2EDTA$, 40 mM $NaHPO_4$, pH 7.2 and 1% SDS at about 40–50° C.; and one other stringent wash is 0.2×SSC and 0.1% SDS at about 50–65° C.

There are also exemplary protocols for stringent washing conditions where oligonucleotide probes are used to screen hybridization media. For example, a first protocol uses 6×SSC with 0.05 percent sodium pyrophosphate at a temperature of between about 35° C. and 63° C., depending on the length of the probe. For example, 14 base probes are washed at 35–40° C., 17 base probes at 45–50° C., 20 base probes at 52–57° C., and 23 base probes at 57–63° C. The temperature can be increased 2–3° C. where background non-specific binding appears high. A second protocol uses tetramethylammonium chloride (TMAC) for washing. One such stringent washing solution is 3 M TMAC, 50 mM Tris-HCl, pH 8.0 and 0.2% SDS.

Another suitable method for obtaining a suitable nucleic acid sequence is the polymerase chain reaction (PCR). In this method, cDNA is prepared from poly(A)+RNA or total RNA using the enzyme reverse transcriptase. Two primers, typically complementary to two separate regions of cDNA (oligonucleotides) encoding the desired protein, are then added to the cDNA along with a polymerase such as Taq polymerase, and the polymerase amplifies the cDNA region between the two primers.

The oligonucleotide sequences selected as probes or primers should be of adequate length and sufficiently unambiguous as to minimize the amount of non-specific binding that may occur during screening or PCR amplification. The actual sequence of the probes or primers is usually based on conserved or highly homologous sequences or regions. Optionally, the probes or primers can be fully or partially degenerate, i.e., can contain a mixture of probes/primers, all encoding the same amino acid sequence but using different codons to do so. An alternative to preparing degenerate probes is to place an inosine in some or all of those codon positions that vary by species. The oligonucleotide probes or primers may be prepared by chemical synthesis methods for DNA, as described above.

Vectors

DNA encoding the desired proteins may be inserted into vectors for further cloning (amplification of the DNA) or for expression. Suitable vectors are commercially available, or the vector may be specifically constructed. The selection or construction of an appropriate vector will depend on (1) whether it is to be used for DNA amplification or for DNA expression, (2) the size of the DNA to be inserted into the vector and (3) the intended host cell to be transformed with the vector.

The vectors each involve a nucleic acid sequence which encodes a desired protein operatively linked to one or more of the following expression control or regulatory sequences capable of directing, controlling or otherwise effecting the expression of a desired protein by a selected host cell. Each vector contains various components, depending on its function (amplification of DNA or expression of DNA) and its compatibility with the intended host cell. The vector components generally include but are not limited to one or more of the following: a signal sequence, an origin of replication, one or more selection or marker genes, a promoter, an enhancer element, a transcription termination sequence and the like. These components may be obtained from natural sources or be synthesized by known procedures.

Examples of suitable prokaryotic cloning vectors include bacteriophages such as lambda derivatives, or plasmids from E. coli (e.g. pBR322, col E1, pUC, the F-factor and Bluescript® plasmid derivatives (Stratagene, LaJolla, Calif.)). Other appropriate expression vectors, of which numerous types are known in the art for the host cells described below, can also be used for this purpose.

Signal Sequence

The nucleic acid encoding a signal sequence may be inserted 5' of the sequence encoding a desired protein, e.g, it may be a component of a vector or it may be a part of a nucleic acid encoding the desired protein. For example, the nucleic acid encoding the native signal sequence of IL-1ra is known (U.S. Pat. No. 5,075,222).

Origin of Replication

Expression and cloning vectors each generally include a nucleic acid sequence that enables the vector to replicate in one or more selected host cells. In a cloning vector, this sequence is typically one that enables the vector to replicate independently of the host chromosomal DNA and includes an origin of replication or autonomously replicating sequence. Such sequences are well known. The origin of replication from the plasmid pBR322 is suitable for most Gram-negative bacteria, and various origins (e.g., SV40, polyoma, adenovirus, VSV or BPV) are useful for cloning vectors in mammalian cells. Generally, the origin of replication is not needed for mammalian expression vectors (for example, the SV40 origin is often used only because it contains the early promoter).

Selection Gene

The expression and cloning vectors each typically contain a selection gene. This gene encodes a "marker" protein necessary for the survival or growth of the transformed host cells when grown in a selective culture medium. Host cells that are not transformed with the vector will not contain the selection gene and, therefore, they will not survive in the culture medium. Typical selection genes encode proteins that (a) confer resistance to antibiotics or other toxins, e.g., ampicillin, neomycin, methotrexate or tetracycline; (b) complement auxotrophic deficiencies or (c) supply critical nutrients not available from the culture medium.

Other selection genes may be used to amplify the genes to be expressed. Amplification is the process wherein genes which are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The cell transformants are placed under selection pressure which only the transformants are uniquely adapted to survive by virtue of the markers present in the vectors. Selection pressure is imposed by culturing the transformed cells under conditions in which the concentration of selection agent in the medium is successively changed, thereby leading to amplification of both the selection gene and the DNA that encodes a desired protein. As a result, increased quantities of a desired protein are synthesized from the amplified DNA.

For example, cells transformed with the DHFR selection gene are first identified by culturing all of the transformants in a culture medium that contains methotrexate, a competitive antagonist of DHFR. An appropriate host cell when wild-type DHFR is used is the Chinese hamster ovary cell line deficient in DHFR activity (Urlaub and Chasin (1980), *Proc. Natl. Acad. Sci., USA,* 77(7):4216–4220, the disclosure of which is hereby incorporated by reference). The transformed cells are then exposed to increased levels of methotrexate. This leads to the synthesis of multiple copies of the DHFR gene and, concomitantly, multiple copies of other DNA present in the expression vector, such as the DNA encoding a desired protein.

Promoter

Expression and cloning vectors each will typically contain a promoter that is recognized by the host organism and is operably linked to a nucleic acid sequence encoding a desired protein. A promoter is an untranslated sequence located upstream (5') to the start codon of a structural gene (generally within about 100 to 1000 bp) that controls the transcription and translation of a particular nucleic acid sequence, such as that encoding a desired protein. A promoter may be conventionally grouped into one of two classes, inducible promoters or constitutive promoters. An inducible promoter initiates increased levels of transcription from DNA under its control in response to some change in culture conditions, such as the presence or absence of a nutrient or a change in temperature. A large number of promoters, recognized by a variety of potential host cells, are well known. A promoter may be operably linked to the DNA encoding a desired protein by removing the promoter from the source DNA by restriction enzyme digestion and inserting the desired promoter sequence. The native IL-1ra promoter sequence may be used to direct amplification and/or expression of the DNA encoding a desired protein. A heterologous promoter is preferred, however, if it permits greater transcription and higher yields of the expressed protein as compared to the native promoter and if it is compatible with the host cell system that has been selected for use. For example, any one of the native promoter sequences of other IL-1 family members may be used to direct amplification and/or expression of the DNA encoding a desired protein.

Promoters suitable for use with prokaryotic hosts include the beta-lactamase and lactose promoter systems; alkaline phosphatase, a tryptophan (trp) promoter system; a bacterial luminescence (luxR) gene system and hybrid promoters such as the tac promoter. Other known bacterial promoters are also suitable. Their nucleotide sequences have been published, thereby enabling one skilled in the art to ligate them to the desired DNA sequence(s) using linkers or adaptors as needed to supply any required restriction sites.

Suitable promoting sequences for use with yeast hosts are also well known in the art. Suitable promoters for use with mammalian host cells are well known and include those obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and, most preferably, Simian Virus 40 (SV40). Other suitable mammalian promoters include heterologous mammalian promoters, e.g., heat-shock promoters and the actin promoter.

Enhancer Element

The expression and cloning vectors each will typically contain an enhancer sequence to increase the transcription by higher eukaryotes of a DNA sequence encoding a desired protein. Enhancers are cis-acting elements of DNA, usually from about 10–300 bp in length, that act on the promoter to increase its transcription. Enhancers are relatively orientation and position independent. They have been found 5' and 3' to the transcription unit. Yeast enhancers are advantageously used with yeast promoters. Several enhancer sequences available from mammalian genes are known (e.g., globin, elastase, albumin, alpha-feto-protein and insulin). Additionally, viral enhancers such as the SV40 enhancer, the cytomegalovirus early promoter enhancer, the polyoma enhancer and adenovirus enhancers are exemplary enhancing elements for the activation of eukaryotic promoters. While an enhancer may be spliced into a vector at a position 5' or 3' to a DNA encoding a desired protein, it is typically located at a site 5' from the promoter.

Transcription Termination

Expression vectors used in eukaryotic host cells each will typically contain a sequence necessary for the termination of transcription and for stabilizing the mRNA. Such sequences are commonly available from the 5' and occasionally 3' untranslated regions of eukaryotic DNAs or cDNAs. These regions contain nucleotide segments transcribed as polyadenylated fragments in the untranslated portion of the mRNA encoding a desired protein.

Vector Construction

The construction of suitable vectors, each containing one or more of the above-listed components (together with the coding sequence encoding a desired protein) may be accomplished by standard ligation techniques. Isolated plasmids or DNA fragments are cleaved, tailored and religated in the desired order to generate the vector required. To confirm that the correct sequence has been constructed, the ligation mixture may be used to transform *E. coli,* and successful transformants may be selected by known techniques as described above. Quantitites of the vector from the transformants are then prepared, analyzed by restriction endonuclease digestion and/or sequenced to confirm the presence of the desired construct.

A vector that provides for the transient expression of DNA encoding a desired protein in mammalian cells may also be used. In general, transient expression involves the use of an expression vector that is able to replicate efficiently in a host cell, such that the host cell accumulates many copies of the expression vector and, in turn, synthesizes high levels of the desired protein encoded by the expression vector. Each transient expression system, comprising a suitable expression vector and a host cell, allows for the convenient positive identification of proteins encoded by cloned DNAs as well as for the rapid screening of such proteins for desired biological or physiological properties, i.e., identifying a biologically-active variant of IL-1ra protein.

Host Cells

Any of a variety of recombinant host cells, each of which contains a nucleic acid sequence for use in expressing a desired protein, is also provided by the present invention. Exemplary prokaryotic and eukaryotic host cells include bacterial, mammalian, fungal, insect, yeast or plant cells.

Prokaryotic host cells include but are not limited to eubacteria such as Gram-negative or Gram-positive organisms (e.g., *E. coli* (HB101, DH5a, DH10 and MC1061); Bacilli, such as *B. subtilis;* Pseudomonas, such as *P. aeruginosa; Streptomyces spp.; Salmonella typhimurium;* or *Serratia marcescans.* As a specific embodiment, a desired protein may be expressed in *E. coli.*

In addition to prokaryotic host cells, eukaryotic microbes such as filamentous fungi or yeast may be suitable hosts for the expression of a desired protein. *Saccharomyces cerevisiae,* or common baker's yeast, is the most commonly used among lower eukaryotic host microorganisms, but a number of other genera, species and strains are well known and commonly available.

A desired protein may be expressed in glycosylated form by any one of a number of suitable host cells derived from multicellular organisms. Such host cells are capable of complex processing and glycosylation activities. In principle, any higher eukaryotic cell culture might be used, whether such culture involves vertebrate or invertebrate cells, including plant and insect cells. As a specific embodiment, a desired protein may be expressed in baculovirus cells.

Vertebrate cells may be used, as the propagation of vertebrate cells in culture (tissue culture) is a well-known procedure. Examples of useful mammalian host cell lines include but are not limited to monkey kidney CV1 line transformed by SV40 (COS-7), human embryonic kidney line (293 cells or 293 cells subcloned for growth in suspension culture), baby hamster kidney cells and Chinese hamster ovary cells. Other suitable mammalian cell lines include but are not limited to HeLa, mouse L-929 cells, 3T3 lines derived from Swiss, Balb-c or NIH mice, and BHK or HaK hamster cell lines. As a specific embodiment, a desired protein may be expressed in COS cells.

A host cell may be transfected and preferably transformed with a desired nucleic acid under appropriate conditions permitting the expression of the nucleic acid sequence. The selection of suitable host cells and methods for transformation, culture, amplification, screening and product production and purification are well known in the art (Gething and Sambrook (1981), *Nature,* 293:620–625 or, alternatively, Kaufman et al. (1985), *Mol. Cell. Biol.,* 5(7) :1750–1759, or U.S. Pat. No. 4,419,446, the disclosures of which are hereby incorporated by reference). For example, for mammalian cells without cell walls, the calcium phosphate precipitation method may be used. Electroporation, micro-injection and other known techniques may also be used.

It is also possible that a desired protein may be produced by homologous recombination or with recombinant production methods utilizing control elements introduced into cells already containing DNA encoding the desired protein. Homologous recombination is a technique originally developed for targeting genes to induce or correct mutations in transcriptionally-active genes (Kucherlapati (1989), *Prog. in Nucl. Acid Res. and Mol. Biol.,* 36:301, the disclosure of which is hereby incorporated by reference). The basic technique was developed as a method for introducing specific mutations into specific regions of the mammalian genome (Thomas et al. (1986), *Cell,* 44:419–428; Thomas and Capecchi (1987), *Cell,* 51:503–512 and Doetschman et al. (1988), *Proc. Natl. Acad. Sci.,* 85:8583–8587, the disclosures of which are hereby incorporated by reference) or to correct specific mutations within defective genes (Doetschman et al. (1987), *Nature,* 330:576–578, the disclosure of which is hereby incorporated by reference). Exemplary techniques are described in U.S. Pat. No. 5,272, 071; WO 92/01069; WO 93/03183; WO 94/12650 and WO 94/31560, the disclosures of which are hereby incorporated by reference.

Through homologous recombination, the DNA sequence to be inserted into the genome can be directed to a specific region of the gene of interest by attaching it to targeting DNA. The targeting DNA is DNA that is complementary (homologous) to a region of the genomic DNA. Small pieces of targeting DNA that are complementary to a specific region of the genome are put in contact with the parental strand during the DNA replication process. A general property of DNA that has been inserted into a cell is to hybridize and therefore recombine with other pieces of endogenous DNA through shared homologous regions. If this complementary strand is attached to an oligonucleotide that contains a mutation or a different sequence of DNA, it too is incorporated into the newly synthesized strand as a result of the recombination. As a result of the proofreading function, it is possible for the new sequence of DNA to serve as the template. Thus, the transferred DNA is incorporated into the genome.

If the sequence of a particular gene is known, such as the nucleic acid sequence of a desired protein, the expression control sequence (a piece of DNA that is complementary to a selected region of the gene) can be synthesized or otherwise obtained, such as by appropriate restriction of the native DNA at specific recognition sites bounding the region of interest. This piece serves as a targeting sequence upon insertion into the cell and will hybridize to its homologous region within the genome. If this hybridization occurs during DNA replication, this piece of DNA, and any additional sequence attached thereto, will act as an Okazaki fragment and will be backstitched into the newly synthesized daughter strand of DNA.

Attached to these pieces of targeting DNA are regions of DNA which may interact with the expression of a desired protein. For example, a promoter/enhancer element, a suppressor or an exogenous transcription modulatory element is inserted into the genome of the intended host cell in proximity and orientation sufficient to influence the transcription of DNA encoding the desired protein. The control element does not encode a desired protein but instead controls a portion of the DNA present in the host cell genome. Thus, the expression of a desired protein may be achieved not by transfection of DNA that encodes a desired protein, but rather by the use of targeting DNA (containing regions of homology with the endogenous gene of interest), coupled with DNA regulatory segments that provide the endogenous gene sequence with recognizable signals for transcription of a desired protein.

Culturing the Host Cells

The method for culturing each of the one or more recombinant host cells for production of a desired protein will vary depending upon many factors and considerations; the optimum production procedure for a given situation will be apparent to those skilled in the art through minimal experimentation. Such recombinant host cells are cultured in a suitable medium and the expressed protein is then optionally recovered, isolated and purified from the culture medium (or from the cell, if expressed intracellularly) by an appropriate means known to those skilled in the art.

Specifically, each of the recombinant cells used to produce a desired protein may be cultured in media suitable for inducing promoters, selecting suitable recombinant host cells or amplifying the gene encoding the desired protein. The media may be supplemented as necessary with hormones and/or other growth factors (such as insulin, transferrin or epidermal growth factor), salts (such as sodium chloride, calcium, magnesium and phosphate), buffers (such as HEPES), nucleosides (such as adenosine and thymidine), antibiotics (such as gentamicin), trace elements (defined as inorganic compounds usually present at final concentrations in the micromolar range), and glucose or another energy source. Other supplements may also be included at appropriate concentrations, as will be appreciated by those skilled in the art. Suitable culture conditions, such as temperature, pH and the like, are also well known to those skilled in the art for use with the selected host cells.

The resulting expression product may then be purified to near homogeneity by using procedures known in the art. Exemplary purification techniques are taught in U.S. Pat. No. 5,075,222, and WO 91/08285. Preferably, expression product is produced in a substantially pure form. By "substantially pure" is meant IL-1ra, in an unmodified form, has a comparatively high specific activity, preferably in the range of approximately 150,000–500,000 receptor units/mg as defined in Hannum et al. (1990), *Nature,* 343:336–340 and Eisenberg et al. (1990), *Nature,* 343:341–346, both of which are specifically incorporated herein by reference. It is to be recognized, however, that a variant of IL-1ra can have a different specific activity.

Pharmaceutical Compositions

Pharmaceutical compositions generally will each typically include a therapeutically effective amount of IL-1ra, a variant of IL-1ra and chemical derivatives thereof (collectively hereinafter referred to as "IL-1ra product") in admixture with one or more pharmaceutically and physiologically acceptable formulation materials. The primary solvent in a vehicle may be either aqueous or non-aqueous in nature.

In addition, the vehicle may contain other pharmaceutically acceptable excipients for modifying or maintaining the pH, preferably between 6.0 and 7.0, more preferably 6.5 (e.g., buffers such as citrates, phosphates and amino acids such glycine); osmolarity (e.g., sucrose, glucose, mannitol and sodium chloride); viscosity; clarity; color; sterility; stability; antioxidants (e.g., sodium sulfite and sodium hydrogen-sulfite); preservatives (e.g., benzoic acid and salicylic acid); odor of the formulation; flavoring and diluting agents; rate of dissolution (e.g., solubilizers or solubilizing agents such as alcohols and polyethylene glycols); rate of release; emulsifying agents; suspending agents; solvents; fillers; bulking agents; delivery vehicles; diluents; excipients and/or pharmaceutical adjuvants. The optimal pharmaceutical formulation for a desired protein will be determined by one skilled in the art depending upon the route of administration and desired dosage (see for example, *Remington's Pharmaceutical Sciences,* 18th Ed. (1990), Mack Publishing Co., Easton, Pa. 18042, pages 1435–1712, the disclosure of which is hereby incorporated by reference). Specific pharmaceutical formulations are as follows: 10 millimolar sodium citrate, 140 millimolar sodium chloride, 0.5 millimolar EDTA, 0.1% polysorbate (w/w) in water, pH6.5 ("citrate buffer formulation"); and 10 millimolar sodium phosphate, 140 millimolar sodium chloride, between 0.1% (wt/wt) and 0.01% polysorbate (w/w) in water, and, optionally, 0.5 millimolar EDTA, pH6.5 ("phosphate buffer formulation").

In a preferred embodiment of the present invention, IL-1ra in the form of finely divided particles is dissolved or suspended in a 0.1–5% w/v solution of hyaluronan or its salt (e.g., sodium hyaluronate) in water or an aqueous solvent (e.g., physiological saline solutions such as a water-soluble sodium salt, 3 to 5% glucose solutions and 3 to 5% xylitol solutions and citrate or phosphate buffer formulations). The hyaluronan and IL-1ra can be mixed using means such as injecting proteinaceous IL-1 inhibitor solution back and forth from one syringe to a second syringe containing a hyaluronan solution, or by stirring, or by microfluidization. The IL-1ra mixtures can be stored at 0–5° C. without degradation or aggregation of the protein. The hyaluronan concentration can range from 0.1–5% w/v, but the preferred concentration is 2%. Likewise, the final IL-1ra concentration in the preparation can be from 0.1–200 mg/ml, but the preferred concentration is 100 mg/ml. The resulting solution or suspension is preferably adjusted so that the pH value is from 6.0 to 7.5.

Once the pharmaceutical compositions have been formulated, each may be stored in a sterile vial as a solution, suspension, gel, emulsion, solid, or a dehydrated or lyophilized powder. Such compositions may be stored either in ready-to-use form or in a form (e.g., lyophilized) requiring reconstitution prior to administration. The preferred storage of such formulations is at temperatures at least as low as 4° C. and preferably at −70° C. It is also preferred that such formulations containing proteinaceous IL-1 inhibitor are stored and administered at or near physiological pH. It is presently believed that storage and administration in a formulation at a high pH (i.e., greater than 8) or at a low pH (i.e., less than 5) is undesirable.

In a specific embodiment, the present invention is directed to kits for producing a single-dose administration unit. The kits may each contain both a first container having a dried protein and a second container having an aqueous formulation. Kits included within the scope of this invention are single and multi-chambered pre-filled syringes; exemplary pre-filled syringes (e.g., liquid syringes, and lyosyringes such as Lyo-Ject®, a dual-chamber pre-filled lyosyringe) are available from Vetter GmbH, Ravensburg, Germany.

IL-1 inhibitors (e.g., IL-1ra products) each may be administered to a patient in therapeutically effective amounts for the treatment of acute and chronic inflammation, such as inflammatory conditions of a joint (e.g., psoriatic arthritis and rheumatoid arthritis). The term "patient" is intended to encompass animals (e.g., cats, dogs and horses) as well as humans.

Further, the IL-1 inhibitor (e.g., preferably IL-1ra product and more preferably IL-1ra) each may be administered via topical, enteral or parenteral administration including, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal, intraventricular and intrasternal injection and infusion. An IL-1 inhibitor (e.g., preferably IL-1ra product and more preferably IL-1ra) may also be administered via oral administration or be administered through mucus membranes, that is, intranasally, sublingually, buccally or rectally for systemic delivery. It is preferred that IL-1 inhibitors (e.g., preferably IL-1ra product and more preferably IL-1ra) are administered via intra-articular, subcutaneous, intramuscular or intravenous injection. By way of example but not limitation, in one specific embodiment IL-1 inhibitors (e.g., preferably IL-1ra product and more preferably IL-1ra) may be administered intra-articularly for the treatment of rheumatoid arthritis and osteoarthritis. By way of example but not limitation in another specific embodiment, IL-1 inhibitors (e.g., preferably IL-1ra product and more preferably IL-1ra) may be administered subcutaneously or intramuscularly for the treatment of rheumatoid arthritis, inflammatory bowel disease, multiple sclerosis, multiple myeloma, or myelogenous (e.g., AML and CML) and other leukemias. By way of example but not limitation, in a still further specific embodiment IL-1 inhibitors (e.g., preferably IL-1ra product and more preferably IL-1ra) may be administered intravenously for the treatment of brain injury as a result of trauma, epilepsy, hemorrhage or stroke, or for the treatment of graft-versus-host disease; or administered intraventricularly for the treatment of brain injury as a result of trauma.

Regardless of the manner of administration, the treatment of IL-1-mediated disease requires a dose or total dose regimen of an IL-1 inhibitor (e.g., preferably IL-1ra product and more preferably IL-1ra) effective to reduce or alleviate symptoms of the disease (e.g., counteract progressive cartilage destruction of a joint as caused by degradation of proteoglycans which are a molecular component of articular cartilage). As hyaluronan and IL-1ra are naturally occurring substances in mammals, it is believed that there is no inherent upper limit to the tolerable dose. However, as in all medicinal treatments, it is prudent to use no more than is necessary to achieve the desired effect.

The specific dose is calculated according to the approximate body weight or surface area of the patient. Other factors in determining the appropriate dosage can include the disease or condition to be treated or prevented, the severity of the disease, the route of administration, and the age, sex and medical condition of the patient. Further refinement of the calculations necessary to determine the appropriate dosage for treatment is routinely made by those skilled in the art, especially in light of the dosage information and assays disclosed herein. The dosage can also be determined through the use of known assays for determining dosages used in conjunction with appropriate dose-response data.

The frequency of dosing depends on the disease and condition of the patient, as well as the pharmacokinetic parameters of the IL-1 inhibitor (e.g., preferably IL-1ra product and more preferably IL-1ra) used in the formulation, and the route of administration. The IL-1 inhibitor (e.g., preferably IL-1ra product and more preferably IL-1ra) may be administered once, or in cases of severe and prolonged disorders, administered daily in less frequent doses or administered with an initial bolus dose followed by a continuous dose or sustained delivery. It is also contemplated that other modes of continuous or near-continuous dosing may be practiced. For example, chemical derivatization may result in sustained release forms which have the effect of a continuous presence in the bloodstream, in predictable amounts based on a determined dosage regimen.

Preferred modes of using IL-1ra products for treatment of acute and chronic inflammatory conditions, including inflammatory conditions of a joint (e.g., rheumatoid arthritis and psoriatic arthritis), are set forth in AU 9173636. These modes include: (1) a single intra-articular injection of IL-1ra given periodically as needed to prevent or remedy the flare-up of arthritis and (2) periodic subcutaneous injections of IL-1ra product. When administered parenterally, the unit dose may be up to 200 mg, generally up to 150 mg and more generally up to 100 mg. When administered into an articular cavity, the pharmaceutical composition is preferably administered as a single injection from a 3 to 10 ml syringe containing a dose up to 200 mg/ml, generally up to 150 mg and more generally up to 100 mg of IL-1 product dissolved in isotonic phosphate buffered saline. The preparation is administered into an articular cavity at a frequency of once every 7 to 10 days. In such a manner, administration is continuously conducted 4 to 5 times while varying the dose if necessary.

Pharmaceutical compositions of the present invention may be administered with other therapeutics suitable for the indication being treated. IL-1 inhibitor product (e.g., preferably IL-1ra product and more preferably IL-1ra) and any of one or more additional anti-inflammatory drugs may be administered separately or in combination. Information regarding the following compounds can be found in "The Merck Manual of Diagnosis and Therapy", Sixteenth Edition, Merck, Sharp & Dohme Research Laboratories, Merck & Co., Rahway, N.J. (1992) and in "Pharmaprojects", PJB Publications Ltd.

Present treatment of acute and chronic inflammation (e.g., inflammatory conditions of a joint such as rheumatoid arthritis) includes first line drugs for control of pain and inflammation, classified as non-steroidal, anti-inflammatory drugs (NSAIDs). Secondary treatments include corticosteroids, slow acting antirheumatic drugs (SAARDs) or disease modifying (DM) drugs.

In a specific embodiment, the present invention is directed to the use of an IL-1 inhibitor (e.g., preferably IL-1ra product and more preferably IL-1ra) and any of one or more NSAIDs for the treatment of acute and chronic inflammation (e.g., inflammatory conditions of a joint such as osteoarthritis, psoriatic arthritis and/or rheumatoid arthritis); and graft versus host disease. NSAIDs owe their anti-inflammatory action, at least in part, to the inhibition of prostaglandin synthesis (Goodman and Gilman in "The Pharmacological Basis of Therapeutics," MacMillan 7th Edition (1985)). NSAIDs can be characterized into nine groups: (1) salicylic acid derivatives; (2) propionic acid derivatives; (3) acetic acid derivatives; (4) fenamic acid derivatives; (5) carboxylic acid derivatives; (6) butyric acid derivatives; (7) oxicams; (8) pyrazoles and (9) pyrazolones.

In a specific embodiment, the present invention is directed to the use of an IL-1 inhibitor (e.g., preferably IL-1ra product and more preferably IL-1ra) with any of one or more salicylic acid derivatives, prodrug esters or pharmaceutically acceptable salts thereof. Such salicylic acid derivatives, prodrug esters and pharmaceutically acceptable salts thereof comprise: acetaminosalol, aloxiprin, aspirin, benorylate, bromosaligenin, calcium acetylsalicylate, choline magnesium trisalicylate diflusinal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide O-acetic acid, salsalate and sulfasalazine. Structurally related salicylic acid derivatives having similar analgesic and anti-inflammatory properties are also intended to be encompassed by this group.

In a specific embodiment, the present invention is directed to the use of an IL-1 inhibitor (e.g., preferably IL-1ra product and more preferably IL-1ra) in combination (pretreatment, post-treatment or concurrent treatment) with any of one or more propionic acid derivatives, prodrug esters or pharmaceutically acceptable salts thereof. The propionic acid derivatives, prodrug esters and pharmaceutically acceptable salts thereof comprise: alminoprofen, benoxaprofen, bucloxic acid, carprofen, dexindoprofen, fenoprofen, flunoxaprofen, fluprofen, flurbiprofen, furcloprofen, ibuprofen, ibuprofen aluminum, ibuproxam, indoprofen, isoprofen, ketoprofen, loxoprofen, miroprofen, naproxen, oxaprozin, piketoprofen, pimeprofen, pirprofen, pranoprofen, protizinic acid, pyridoxiprofen, suprofen, tiaprofenic acid and tioxaprofen. Structurally related propionic acid derivatives having similar analgesic and anti-inflammatory properties are also intended to be encompassed by this group.

In a specific embodiment, the present invention is directed to the use of an IL-1 inhibitor (e.g., preferably IL-1ra product and more preferably IL-1ra) in combination (pretreatment, post-treatment or concurrent treatment) with any of one or more acetic acid derivatives, prodrug esters or pharmaceutically acceptable salts thereof. The acetic acid derivatives, prodrug esters and pharmaceutically acceptable salts thereof comprise: acemetacin, alclofenac, amfenac, bufexamac, cinmetacin, clopirac, delmetacin, diclofenac sodium, etodolac, felbinac, fenclofenac, fenclorac, fenclozic acid, fentiazac, furofenac, glucametacin, ibufenac, indomethacin, isofezolac, isoxepac, lonazolac, metiazinic acid, oxametacin, oxpinac, pimetacin, proglumetacin, sulindac, talmetacin, tiaramide, tiopinac, tolmetin, zidometacin and zomepirac. Structurally related acetic acid derivatives having similar analgesic and anti-inflammatory properties are also intended to be encompassed by this group.

In a specific embodiment, the present invention is directed to the use of an IL-1 inhibitor (e.g., preferably IL-1ra product and more preferably IL-1ra) in combination (pretreatment, post-treatment or concurrent treatment) with any of one or more fenamic acid derivatives, prodrug esters or pharmaceutically acceptable salts thereof. The fenamic acid derivatives, prodrug esters and pharmaceutically acceptable salts thereof comprise: enfenamic acid, etofenamate, flufenamic acid, isonixin, meclofenamic acid, meclofenamate sodium, medofenamic acid, mefanamic acid, niflumic acid, talniflumate, terofenamate, tolfenamic acid and ufenamate. Structurally related fenamic acid derivatives having similar analgesic and anti-inflammatory properties are also intended to be encompassed by this group.

In a specific embodiment, the present invention is directed to the use of an IL-1 inhibitor (e.g., preferably IL-1ra product and more preferably IL-1ra) in combination (pretreatment, post-treatment or concurrent treatment) with any of one or more carboxylic acid derivatives, prodrug esters or pharmaceutically acceptable salts thereof. The carboxylic acid derivatives, prodrug esters and pharmaceutically acceptable salts thereof which can be used comprise: clidanac, diflunisal, flufenisal, inoridine, ketorolac and tinoridine. Structurally related carboxylic acid derivatives having similar analgesic and anti-inflammatory properties are also intended to be encompassed by this group.

In a specific embodiment, the present invention is directed to the use of an IL-1 inhibitor (e.g., preferably IL-1ra product and more preferably IL-1ra) in combination (pretreatment, post-treatment or concurrent treatment) with any of one or more butyric acid derivatives, prodrug esters or pharmaceutically acceptable salts thereof. The butyric acid derivatives, prodrug esters and pharmaceutically acceptable salts thereof comprise: bumadizon, butibufen, fenbufen and xenbucin. Structurally related butyric acid derivatives having similar analgesic and anti-inflammatory properties are also intended to be encompassed by this group.

In a specific embodiment, the present invention is directed to the use of an IL-1 inhibitor (e.g., preferably IL-1ra product and more preferably IL-1ra) in combination (pretreatment, post-treatment or concurrent treatment) with any of one or more oxicams, prodrug esters or pharmaceutically acceptable salts thereof. The oxicams, prodrug esters and pharmaceutically acceptable salts thereof comprise: droxicam, enolicam, isoxicam, piroxicam, sudoxicam, tenoxicam and 4-hydroxyl-1,2-benzothiazine 1,1-dioxide 4-(N-phenyl)-carboxamide. Structurally related oxicams having similar analgesic and anti-inflammatory properties are also intended to be encompassed by this group.

In a specific embodiment, the present invention is directed to the use of an IL-1 inhibitor (e.g., preferably IL-1ra product and more preferably IL-1ra) in combination (pretreatment, post-treatment or concurrent treatment) with any of one or more pyrazoles, prodrug esters or pharmaceutically acceptable salts thereof. The pyrazoles, prodrug esters and pharmaceutically acceptable salts thereof which may be used comprise: difenamizole and epirizole. Structurally related pyrazoles having similar analgesic and anti-inflammatory properties are also intended to be encompassed by this group.

In a specific embodiment, the present invention is directed to the use of an IL-1 inhibitor (e.g., preferably IL-1ra product and more preferably IL-1ra) in combination (pretreatment, post-treatment or concurrent treatment) with any of one or more pyrazolones, prodrug esters or pharmaceutically acceptable salts thereof. The pyrazolones, prodrug esters and pharmaceutically acceptable salts thereof which may be used comprise: apazone, azapropazone, benzpiperylon, feprazone, mofebutazone, morazone, oxyphenbutazone, phenylbutazone, pipebuzone, propylphenazone, ramifenazone, suxibuzone and thiazolinobutazone. Structurally related pyrazalones having similar analgesic and anti-inflammatory properties are also intended to be encompassed by this group.

In a specific embodiment, the present invention is directed to the use of an IL-1 inhibitor (e.g., preferably IL-1ra product and more preferably IL-1ra) in combination (pretreatment, post-treatment or concurrent treatment) with any of one or more of the following NSAIDs: $\epsilon$-acetamidocaproic acid, S-adenosylmethionine, 3-amino-4-hydroxybutyric acid, amixetrine, anitrazafen, antrafenine, bendazac, bendazac lysinate, benzydamine, beprozin, broperamole, bucolome, bufezolac, ciproquazone, cloximate, dazidamine, deboxamet, detomidine, difenpiramide, difenpyramide, difisalamine, ditazol, emorfazone, fanetizole mesylate, fenflumizole, floctafenine, flumizole, flunixin, fluproquazone, fopirtoline, fosfosal, guaimesal, guaiazolene, isonixirn, lefetamine HCl, leflunomide, lofemizole, lotifazole, lysin clonixinate, meseclazone, nabumetone, nictindole, nimesulide, orgotein, orpanoxin, oxaceprolm, oxapadol, paranyline, perisoxal, perisoxal citrate, pifoxime, piproxen, pirazolac, pirfenidone, proquazone, proxazole, thielavin B, tiflamizole, timegadine, tolectin, tolpadol, tryptamid and those designated by company code number such as 480156S, AA861, AD1590, AFP802, AFP860, AI77B, AP504, AU8001, BPPC, BW540C, CHINOIN 127, CN100, EB382, EL508, F1044, FK-506, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301 and WY41770. Structurally related NSAIDs having similar analgesic and anti-inflammatory properties to the above NSAIDs are also intended to be encompassed by this group.

In a specific embodiment, the present invention is directed to the use of an IL-1 inhibitor (e.g., preferably IL-1ra product and more preferably IL-1ra) in combination (pretreatment, post-treatment or concurrent treatment) with any of one or more corticosteroids, prodrug esters or pharmaceutically acceptable salts thereof for the treatment of acute and chronic inflammation (e.g., inflammatory conditions of a joint such as osteoarthritis, psoriatic arthritis and/or rheumatoid arthritis); graft versus host disease and multiple sclerosis. Corticosteroids, prodrug esters and pharmaceutically acceptable salts thereof include hydrocortisone and compounds which are derived from hydrocortisone, such as 21-acetoxypregnenolone, alclomerasone, algestone, amcinonide, beclomethasone, betamethasone, betamethasone valerate, budesonide, chloroprednisone, clobetasol, clobetasol propionate, clobetasone, clobetasone butyrate, clocortolone, cloprednol, corticosterone, cortisone, cortivazol, deflazacon, desonide, desoximerasone, dexamethasone, diflorasone, diflucortolone, difluprednate, enoxolone, fluazacort, flucloronide, flumethasone, flumethasone pivalate, flunisolide, flucinolone acetonide, fluocinonide, fluorocinolone acetonide, fluocortin butyl, fluocortolone, fluorocortolone hexanoate, diflucortolone valerate, fluorometholone, fluperolone acetate, fluprednidene acetate, fluprednisolone, flurandenolide, formocortal, halcinonide, halometasone, halopredone acetate, hydrocortamate, hydrocortisone, hydrocortisone acetate, hydrocortisone butyrate, hydrocortisone phosphate, hydrocortisone 21-sodium succinate, hydrocortisone tebutate, mazipredone, medrysone, meprednisone, methylprednicolone, mometasone furoate, paramethasone, prednicarbate, prednisolone, prednisolone 21-diedryaminoacetate, prednisolone sodium phosphate, prednisolone sodium succinate, prednisolone sodium 21-m-sulfobenzoate, prednisolone sodium 21-stearoglycolate, prednisolone tebutate, prednisolone 21-trimethylacetate, prednisone, prednival, prednylidene, prednylidene 21-diethylaminoacetate, tixocortol, triamcinolone, triamcinolone acetonide, triamcinolone benetonide and triamcinolone hexacetonide. Structurally related corticosteroids having similar analgesic and anti-inflammatory properties are also intended to be encompassed by this group.

In a specific embodiment, the present invention is directed to the use of an IL-1 inhibitor (e.g., preferably IL-1ra product and more preferably IL-1ra) in combination (pretreatment, post-treatment or concurrent treatment) with any of one or more slow-acting antirheumatic drugs (SAARDs) or disease modifying antirheumatic drugs (DMARDS), prodrug esters or pharmaceutically acceptable salts thereof for the treatment of acute and chronic inflammation (e.g., inflammatory conditions of a joint such as for the treatment of acute and chronic inflammation (e.g., inflammatory conditions of a joint such as osteoarthritis, psoriatic arthritis and/or rheumatoid arthritis); graft versus host disease and multiple sclerosis. SAARDs or DMARDS, prodrug esters and pharmaceutically acceptable salts thereof comprise: allocupreide sodium, auranofin, aurothioglucose, aurothioglycanide, azathioprine, brequinar sodium, bucillamine, calcium 3-aurothio-2-propanol-1-sulfonate, chlorambucil, chloroquine, clobuzarit, cuproxoline, cyclophosphamide, cyclosporin, dapsone, 15-deoxyspergualin, diacerein, glucosamine, gold salts (e.g., cycloquine gold salt, gold sodium thiomalate, gold sodium thiosulfate), hydroxychloroquine, hydroxyurea, kebuzone, levamisole, lobenzarit, melittin, 6-mercaptopurine, methotrexate, mizoribine, mycophenolate mofetil, myoral, nitrogen mustard, D-penicillamine, pyridinol imidazoles such as SKNF86002 and SB203580, rapamycin, thiols, thymopoietin and vincristine. Structurally related SAARDs or DMARDs having similar analgesic and anti-inflammatory properties are also intended to be encompassed by this group.

In a specific embodiment, the present invention is directed to the use of an IL-1 inhibitor (e.g., preferably IL-1ra product and more preferably IL-1ra) in combination (pretreatment, post-treatment or concurrent treatment) with any of one or more COX2 inhibitors, their prodrug esters or pharmaceutically acceptable salts thereof for the treatment of acute and chronic inflammation. Examples of COX2 inhibitors, prodrug esters or pharmaceutically acceptable salts thereof include, for example, celecoxib. Structurally related COX2 inhibitors having similar analgesic and anti-inflammatory properties are also intended to be encompassed by this group.

In a specific embodiment, the present invention is directed to the use of an IL-1 inhibitor (e.g., preferably IL-1ra product and more preferably IL-1ra) in combination (pretreatment, post-treatment or concurrent treatment) with any of one or more antimicrobials, prodrug esters or pharmaceutically acceptable salts thereof for the treatment of acute and chronic inflammation. Antimicrobials, prodrug esters and pharmaceutically acceptable salts thereof include, for example, ampicillin, amoxycillin, aureomicin, bacitracin, ceftazidime, ceftriaxone, cefotaxime, cephachlor, cephalexin, cephradine, ciprofloxacin, clavulanic acid, cloxacillin, dicloxacillan, erythromycin, flucloxacillan, gentamicin, gramicidin, methicillan, neomycin, oxacillan, penicillin and vancomycin. Structurally related antimicrobials having similar analgesic and anti-inflammatory properties are also intended to be encompassed by this group.

In a specific embodiment, the present invention is directed to the use of an IL-1 inhibitor (e.g., preferably IL-1ra product and more preferably IL-1ra) in combination (pretreatment, post-treatment or concurrent treatment) with any of one or more TNF inhibitors for the treatment of acute and chronic inflammation (e.g., inflammatory conditions of a joint such as osteoarthritis, psoriatic arthritis and/or rheumatoid arthritis); brain injury as a result of trauma, epilepsy, hemorrhage or stroke; and graft versus disease. Such TNF inhibitors include compounds and proteins which block in vivo synthesis or extracellular release of TNF. In a specific embodiment, the present invention is directed to the use of an IL-1 inhibitor (e.g., preferably IL-1ra product and more preferably IL-1ra) in combination (pretreatment, post-treatment or concurrent treatment) with any of one or more of the following TNF inhibitors: TNF binding proteins (soluble TNF receptors), anti-TNF antibodies, granulocyte colony stimulating factor; thalidomide; BN 50730; tenidap; E 5531; tiapafant PCA 4248; nimesulide; panavir; rolipram; RP 73401; peptide T, MDL 201,449A; (1R,3S)-Cis-1-[9-(2, 6-diaminopurinyl)]-3-hydroxy-4-cyclopentene hydrochloride; (1R,3R)-trans-1-[9-(2,6-diamino)purine]-3-acetoxycyclopentane; (1R,3R)-trans-1-[9-adenyl)-3-azidocyclopentane hydrochloride and (1R,3R)-trans-1-[6-hydroxy-purin-9-yl)-3-azidocyclopentane.

TNF binding proteins are disclosed in the art (EP 308 378, EP 422 339, GB 2 218 101, EP 393 438, WO 90/13575, EP 398 327, EP 412 486, WO 91/03553, EP 418 014, JP 127,800/1991, EP 433 900, U.S. Pat. No. 5,136,021, GB 2 246 569, EP 464 533, WO 92/01002, WO 92/13095, WO 92/16221, EP 512 528, EP 526 905, WO 93/07863, EP 568 928, WO 93/21946, WO 93/19777, EP 417 563, U.S. Provisional patent application Ser. No. 60/021,443, filed Jul. 9, 1996 by Fisher, Edwards and Kieft, entitled on the Provisional Application transmittal letter as "TUMOR NECROSIS FACTOR BINDING PROTEINS" (Attorney Docket No. A-415P), U.S. Provisional patent application Ser. No. 60/036,534, filed on Dec. 6, 1996 by Fisher, Edwards and Kieft, entitled on the Provisional Application transmittal letter as "LOW MOLECULAR WEIGHT TUMOR NECROSIS FACTOR BINDING PROTEINS" (Attorney Docket No. A-415A-P), U.S. Provisional patent application Ser. No. 60/037,737, filed on Jan. 23, 1997 by Fisher, Edwards and Kieft, entitled on the Provisional Application transmittal letter as "LOW MOLECULAR WEIGHT TUMOR NECROSIS FACTOR BINDING PROTEINS" (Attorney Docket No. A-415B-P),and U.S. Provisional patent application Ser. No. 60/039,314, filed on Feb. 7, 1997 by Fisher, Edwards and Kieft, entitled on the Provisional Application transmittal letter as "LOW MOLECULAR WEIGHT TUMOR NECROSIS FACTOR BINDING PROTEINS" (Attorney Docket No. A-415C-P), the disclosures of which are hereby incorporated by reference).

For example, EP 393 438 and EP 422 339 teach the amino acid and nucleic acid sequences of a "30 kDa TNF inhibitor" (also known as the p55 receptor) and a "40 kDa inhibitor" (also known as the p75 receptor) as well as modified forms thereof (e.g., fragments, functional derivatives and variants). EP 393 438 and EP 422 339 also disclose methods for isolating the genes responsible for coding the inhibitors, cloning the gene in suitable vectors and cell types and expressing the gene to produce the inhibitors. Additionally, polyvalent forms (i.e., molecules comprising more than one active moiety) of the above-described TNF inhibitors have also been disclosed. In one embodiment, the polyvalent form may be constructed, for example, by chemically coupling at least one TNF inhibitor and another moiety with any clinically acceptable linker, for example polyethylene glycol (WO 92/16221 and WO 95/34326), by a peptide linker (Neve et al. (1996), *Cytokine*, 8(5):365–370) by chemically coupling to biotin and then binding to avidin (WO 91/03553) and, finally, by constructing chimeric antibody molecules (U.S. Pat. No. 5,116,964, WO 89/09622, WO 91/16437 and EP 315062).

Anti-TNF antibodies include MAK 195F Fab antibody (Holler et al. (1993), 1st International Symposium on Cytokines in Bone Marrow Transplantation, 147); CDP 571 anti-TNF monoclonal antibody (Rankin et al. (1995), *British Journal of Rheumatology*, 34:334–342); BAY X 1351 murine anti-tumor necrosis factor monoclonal antibody (Kieft et al. (1995), 7th European Congress of Clinical Microbiology and Infectious Diseases, 9); CenTNF cA2 anti-TNF monoclonal antibody (Elliott et al. (1994), *Lancet*, 344:1125–1127 and Elliott et al. (1994), *Lancet*, 344:1105–1110).

In a specific embodiment, the present invention is directed to the use of an IL-1 inhibitor (e.g., preferably IL-1ra product and more preferably IL-1ra) in combination (pretreatment, post-treatment or concurrent treatment) with the soluble recombinant human Fas antigen or recombinant versions thereof for the treatment of acute and chronic inflammation (e.g., inflammatory conditions of a joint such as osteoarthritis, psoriatic arthritis and/or rheumatoid arthritis); and graft versus host disease. Soluble recombinant human Fas antigen, and variants thereof such as a fas fusion protein, methods for isolating the genes responsible for coding the soluble recombinant human Fas antigen, methods for cloning the gene in suitable vectors and cell types, and methods for expressing the gene to produce the inhibitors are known (WO 96/20206 and Mountz et al., *J. Immunology*, 155:4829–4837, the disclosures of which are hereby incorporated by reference).

The above is by way of example and does not preclude other treatments to be used concurrently with these anti-arthritic compounds that are known by those skilled in the art or that could be arrived at by those skilled in the art using the guidelines set forth in this specification.

It is especially advantageous to formulate compositions of the additional anti-inflammatory compounds in dosage unit form for ease of administration and uniformity of dosage. "Dosage unit form" as used herein refers to physically discrete units suited as unitary dosages for the mammalian subjects to be treated, each unit containing a predetermined quantity of additional anti-inflammatory compounds calculated to produce the desired therapeutic effect in association with the required pharmaceutical carrier. As used herein, "pharmaceutically acceptable carrier" includes any and all solvents, dispersion media, coating, antibacterial and antifungal agents, isotonic and absorption delaying agents and the like which are compatible with the active ingredient and with the mode of administration and other ingredients of the formulation and not deleterious to the recipient. The use of such media and agents is well known in the art (see for example, *Remington's Pharmaceutical Sciences*, 18th Ed. (1990), Mack Publishing Co., Easton, Pa. 18042, pages 1435–1712). An exemplary pharmaceutically acceptable carrier is phosphate buffered saline. Supplementary active ingredients can also be incorporated into the compositions.

For oral therapeutic administration, the additional anti-inflammatory compound may be incorporated with excipients and used in the form of ingestible tablets, buccal tablets, troches, capsules, elixers, suspensions, syrups, wafers and the like, or it may be incorporated directly with the food in the diet. The tablets, troches, pills, capsules and the like may also contain the following: a binder such as gum tragacanth, acacia, corn starch or gelatin; excipients such as dicalcium phosphate; a disintegrating agent such as corn starch, alginic acid and the like; a lubricant such as magnesium stearate; a sweetening agent such as sucrose, lactose or saccharin; or a flavoring agent such as peppermint, oil of wintergreen or cherry or orange flavoring. When the dosage unit form is a capsule, it may contain, in addition to material of the above type, a liquid carrier. Various other materials may be present as a coating or to otherwise modify the physical form of the dosage unit. For instance, tablets, pills or capsules may be coated with shellac, sugar or both. Of course, any material used in preparing any dosage unit form should be pharmaceutically pure and substantially non-toxic in the amounts employed. In addition, the additional anti-inflammatory compound may be incorporated into a sustained-release preparation and formulation. The amount of the additional anti-inflammatory compound in such a therapeutically useful composition is such that a suitable dosage will be obtained.

For parenteral therapeutic administration, each anti-inflammatory compound may be incorporated with a sterile injectable solution. The sterile injectable solution may be prepared by incorporating the additional anti-inflammatory compound in the required amount in an appropriate pharmaceutically acceptable carrier, with various other ingredients enumerated below (required), followed by filtered sterilization. In the case of dispersions, each may be prepared by incorporating the additional anti-inflammatory compound into a sterile vehicle which contains the basic dispersion medium and the required other ingredients from those enumerated above. In the case of sterile injectable solutions, each may be prepared by incorporating a powder of at least one additional anti-inflammatory compound and, optionally, any additional desired ingredient from a previously sterile-filtered solution thereof, wherein the powder is prepared by any suitable technique (e.g., vacuum drying and freeze drying).

The specific dose of the additional anti-inflammatory compound is calculated according to the approximate body weight or surface area of the patient. Other factors in determining the appropriate dosage can include the acute or chronic inflammatory disease or condition to be treated or prevented, the severity of the disease, the route of administration, and the age, sex and medical condition of the patient. Further refinement of the calculations necessary to determine the appropriate dosage for treatment involving each of the above-mentioned formulations is routinely made by those skilled in the art. Dosages can also be determined through the use of known assays for determining dosages used in conjunction with appropriate dose-response data.

Thus, for example, it is within the scope of the invention that doses of the additional anti-inflammatory compounds selected for treating a particular acute or chronic inflammatory disease can be varied to achieve a desired therapeutic effect. Where one of the additional anti-inflammatory compounds has side effects, it can be given to patients during alternate treatment periods. For example, chronic methotrexate treatment is associated with gastrointestinal, hepatic, bone marrow and pulmonary toxicity (Sandoval et al. (1995), *British Journal of Rheumatology,* 34:49–56).

Tests for monitoring the improvement of a disease can include specific tests directed, for example, to the determination of systemic response to inflammation, which include the erythrocyte sedimentation rate (ESR) and acute phase reactants (APR). Observations are made of the swelling, etc. of the afflicted body parts. Improvement in stiffness, and grip (where applicable), and reduction in pain of the patient is also observed. If the patient's condition is stable, he is re-treated at the same dosage weekly and is evaluated weekly. Provided the patient's condition is stable, the treatment may be continued. After six months of treatment, anatomical changes of the skeleton are determined by radiologic imaging, for example by X-radiography.

At the end of each period, the patient is again evaluated. Comparison of the pre-treatment and post-treatment radiological assessment, ESR and APR indicates the efficacy of the treatments. According to the efficacy of the treatments and the patient's condition, the dosage may be increased or maintained constant for the duration of treatment.

Preferably, the present invention is directed to a method comprising the use of one of the following combinations to treat or prevent an acute or chronic inflammatory disease and condition, as defined above, such as inflammatory conditions of a joint (e.g., psoriatic arthritis and rheumatoid arthritis) and the symptoms associated therewith: IL-1ra product (e.g., IL-1ra) and methotrexate; IL-1ra product (e.g., IL-1ra) and any one or more of methotrexate, sulphasazine and hydroxychloroquine; IL-1ra product (e.g., IL-1ra), methotrexate and hydroxychloroquine; IL-1ra product (e.g., IL-1ra), methotrexate and sulphasazine; and IL-1ra product (e.g., IL-1ra), methotrexate and a TNF inhibitor, preferably TNFbp.

In a specific preferred embodiment, the method comprises the administration (e.g., intra-articular, subcutaneous or intramuscular) of IL-1 inhibitor (e.g., preferably IL-1ra product and more preferably IL-1ra, formulated with a controlled release polymer (e.g., hyaluronan)) optionally in combination (pretreatment, post-treatment or concurrent treatment) with methotrexate and/or TNFbp to treat arthritis (e.g., osteoarthritis, psoriatic arthritis and/or rheumatoid arthritis) and the symptoms associated therewith.

In a specific preferred embodiment, the method comprises the administration (e.g., intravenous or intraventricular) of an IL-1 inhibitor (e.g., preferably IL-1ra product and more preferably IL-1ra, formulated with a controlled release polymer (e.g., hyaluronan)) optionally in combination (pretreatment, post-treatment or concurrent treatment) with tissue plasminogen activator and/or TNFbp to treat brain injury as a result of trauma, epilepsy, hemorrhage or stroke, each of which may lead to neurodegeneration.

In a specific preferred embodiment, the method comprises the administration (e.g., subcutaneous or intramuscular) of an IL-1 inhibitor (e.g., preferably IL-1ra product and more preferably IL-1ra, formulated with a controlled release polymer (e.g., hyaluronan)) optionally in combination (pretreatment, post-treatment or concurrent treatment) with one or more of a corticosteroid, cyclosporin, an interferon (e.g., alpha interferon, beta interferon, gamma interferon or consensus interferon) and/or TNFbp to treat multiple sclerosis.

In a specific preferred embodiment, the method comprises the administration (e.g., intravenous) of an IL-1 inhibitor (e.g., preferably IL-1ra product and more preferably IL-1ra, formulated with a controlled release polymer (e.g., hyaluronan)) optionally in combination (pretreatment, post-treatment or concurrent treatment) with one or more of methotrexate, a corticosteroid, FK-506, cyclosporin, a soluble fas protein and/or TNFbp to treat graft versus host disease.

In a specific preferred embodiment, the method comprises the administration (e.g., subcutaneous or intramuscular) of an IL-1 inhibitor (e.g., preferably IL-1ra product and more preferably IL-1ra, formulated with a controlled release polymer (e.g., hyaluronan)) optionally in combination (pretreatment, post-treatment or concurrent treatment) with G-CSF and/or TNFbp to treat inflammatory bowel disease.

In a specific preferred embodiment, the method comprises the administration (e.g., subcutaneous or intramuscular) of an IL-1 inhibitor (e.g., preferably IL-1ra product and more preferably IL-1ra, formulated with a controlled release polymer (e.g., hyaluronan)) optionally in combination (pretreatment, post-treatment or concurrent treatment) with an interferon (e.g., alpha interferon, beta interferon, gamma interferon or consensus interferon) to treat multiple myeloma or myelogenous (e.g., AML and CML) and other leukemias.

In a specific preferred embodiment, the method comprises the administration (e.g., subcutaneous, intraventricular or intrathecal) of an IL-1 inhibitor (e.g., preferably IL-1ra product and more preferably IL-1ra, formulated with a controlled release polymer (e.g., hyaluronan)) optionally in combination (pretreatment, post-treatment or concurrent treatment) with an NSAID (e.g., indomethacin) and/or TNFbp to treat Alzheimer's disease.

In a specific preferred embodiment, the method comprises the administration (e.g., local injection, subcutaneous or intramuscular) of an IL-1 inhibitor (e.g., preferably IL-1ra product and more preferably IL-1ra, formulated with a controlled release polymer (e.g., hyaluronan)) to treat temporal mandibular joint disease.

The following examples are included to more fully illustrate the present invention. It is understood that modifications can be made in the procedures set forth without departing from the spirit of the invention.

EXAMPLES

Standard methods for many of the procedures described in the following examples, or suitable alternative procedures, are provided in widely recognized manuals of molecular biology such as, for example, Sambrook et al., Molecular Cloning, Second Edition, Cold Spring Harbor Laboratory Press (1987) and Ausabel et al., *Current Protocols in Molecular Biology,* Greene Publishing Associates/Wiley Interscience, New York (1990). All chemicals were either analytical grade or USP grade.

Example 1

Sample Preparation: Various concentrations of hyaluronic acid were prepared in PBS from lyophilized material in a 3–10 ml syringe. The syringe containing the hyaluronic acid was then attached by means of a stopcock to a syringe containing proteinaceous IL-1 inhibitor in 10 millimolar sodium citrate, 140 millimolar sodium chloride, 0.5 millimolar EDTA, 0.1% polysorbate (w/w) in water, pH6.5. The two solutions were then mixed by injecting the proteinaceous IL-1 inhibitor solution into the hyaluronic acid solution and injecting the contents back and forth several times to ensure mixing.

An *E. coli*-derived human recombinant IL-1 receptor antagonist (prepared generally in accordance with the teachings of U.S. Pat. No. 5,075,222, rhuIL-1ra) was formulated in H-10™ hylan fluid, a cross-linked hyaluronic acid (Biomatrix, Inc., Ridgefield, Inc.) to achieve a 100 mg/ml IL-1ra and 2% hyaluronic acid ($Mr \geq 4 \times 10^6$) in PBS. The IL-1ra/hyaluronic acid mixture was injected subcutaneously into rats. At various times after injection, blood was drawn via catheters inserted into the jugular veins of the animals. The blood was centrifuged to remove blood cells and the remaining plasma was assayed for IL-1ra using an ELISA kit (Quantikine™ human IL-1ra immunoassay, R&D Systems, Minneapolis, Minn.) according to the manufacturer's guidelines. The data are expressed as plasma IL-1ra ($\mu$g/ml IL-1ra in plasma) vs. time after injection, as shown in Table 2 and FIG. 1.

TABLE 2

Plasma IL-1ra after Subcutaneous Injection

| Time after Injection (Hours) | Plasma IL-1ra ($\mu$g/ml) IL-1ra alone | IL-1ra (100 mg/ml)/ hyaluronic acid (2% w/v) |
|---|---|---|
| 0 | 3 ± 14 | 1 ± 0 |
| 0.08 | 343 ± 5 | 134 ± 0 |
| 0.17 | 343 ± 5 | 133 ± 1 |
| 0.5 | 344 ± 2 | 134 ± 1 |
| 1 | 339 ± 8 | 133 ± 0 |
| 2 | 344 ± 5 | 132 ± 1 |
| 4 | 339 ± 8 | 133 ± 2 |
| 8 | 346 ± 8 | 134 ± 3 |
| 12 | 315 ± 47 | 135 ± 2 |
| 24 | 200 ± 30 | 135 ± 2 |
| 36 | 45 ± 12 | 135 ± 2 |
| 48 | 5 ± 5 | 106 ± 37 |
| 72 | 2 ± 2 | 12 ± 6 |
| 96 | 0.2 ± 7 | 2 ± 1 |

As shown in Table 2 and FIG. 1, incorporation of IL-1ra into hyaluronic acid leads to prolonged elevation of IL-1ra plasma levels as compared to IL-1ra administered in the absence of hyaluronic acid.

Example 2

Figure 2:
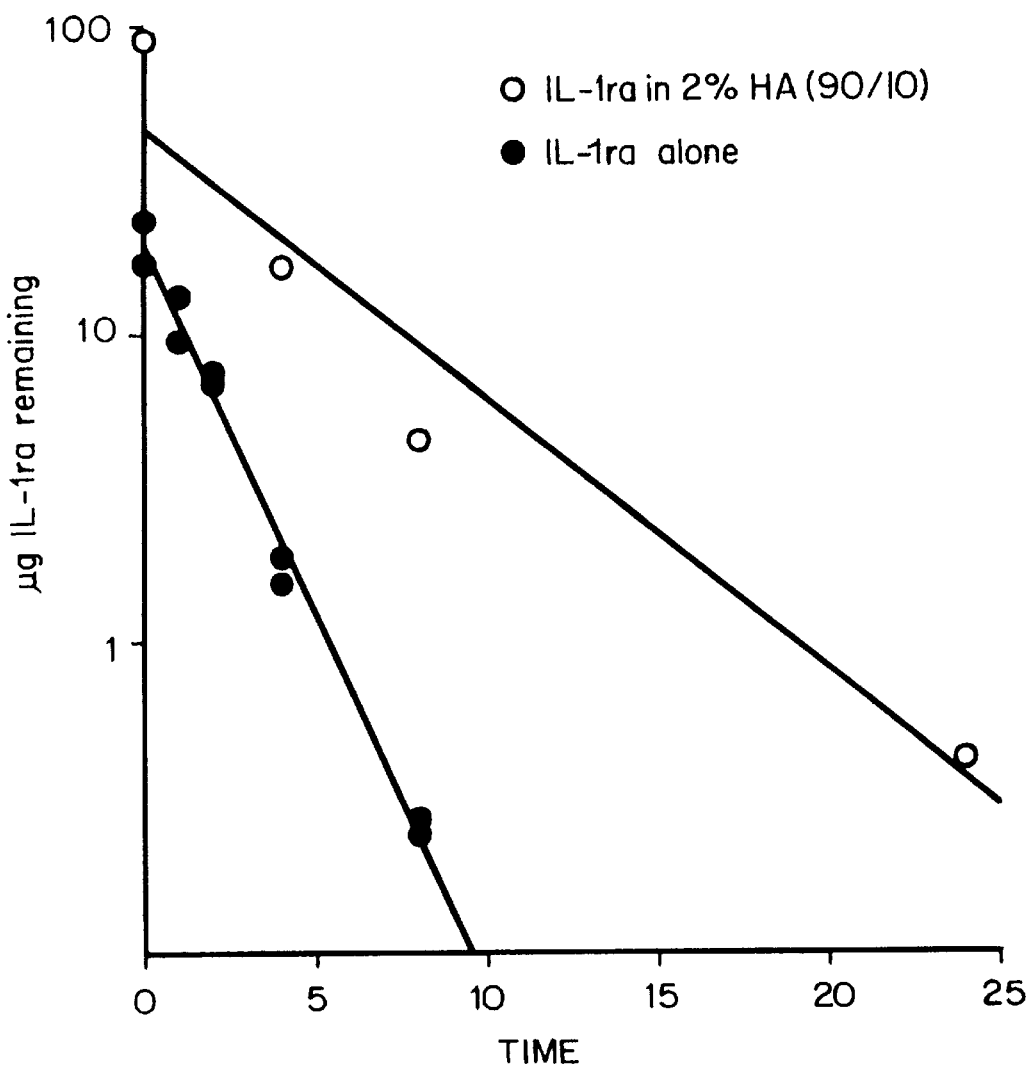
FIG. 2 shows the amount of IL-1ra remaining in guinea pig joints after intra-articular injection of either IL-1ra alone or IL-1ra mixed with hyaluronic acid.

IL-1ra was radiolabeled with Na[$^{125}$I], and then incorporated into hyaluronic acid (2% final), as described above. Radioactive IL-1ra or IL-1ra/hyaluronic acid mixtures were injected intra-articularly into the hind knees of guinea pigs. At various times after injection, the animals were sacrificed and the knee joints removed and counted in a gamma counter, as described in van Lent et al. (1989), *J. Rheumatol.,* 16:1295–1303. The amount of IL-1ra remaining in the joints at each time point is shown in FIG. 2. The intra-articular half lives of IL-1ra in three different hyaluronic acid formulations were calculated from graphs such as FIG. 2, and are shown in Table 3.

TABLE 3

Joint Half-life of IL-1ra Formulations in Guinea Pigs after Intra-articular Injection

| Formulation[a] | Ratio[b] | Half-life (hours |
|---|---|---|
| IL-1ra alone | NA | 1.36 |
| IL-1ra/hyaluronic acid | 90/10 | 3.54 |
| IL-1ra/hyaluronic acid | 80/20 | 2.45 |
| IL-1ra/hyaluronic acid | 50/50 | 1.45 |

[a]IL-1ra concentration 100 mg/ml. When applicable, hyaluronic acid concentration 2% (w/v).
[b]Ratio of fluid (non-crosslinked) to gel (cross-linked) hyaluronic acid in formulation.

As shown in Table 3 and FIG. 2, incorporation of IL-1ra into hyaluronic acid leads to prolonged retention of IL-1ra in knee joints after intra-articular administration. The degree of retention can be controlled by the ratio of crosslinked (gel) to non-crosslinked (fluid) hyaluronic acid in the formulation.

Example 3

Figure 3:
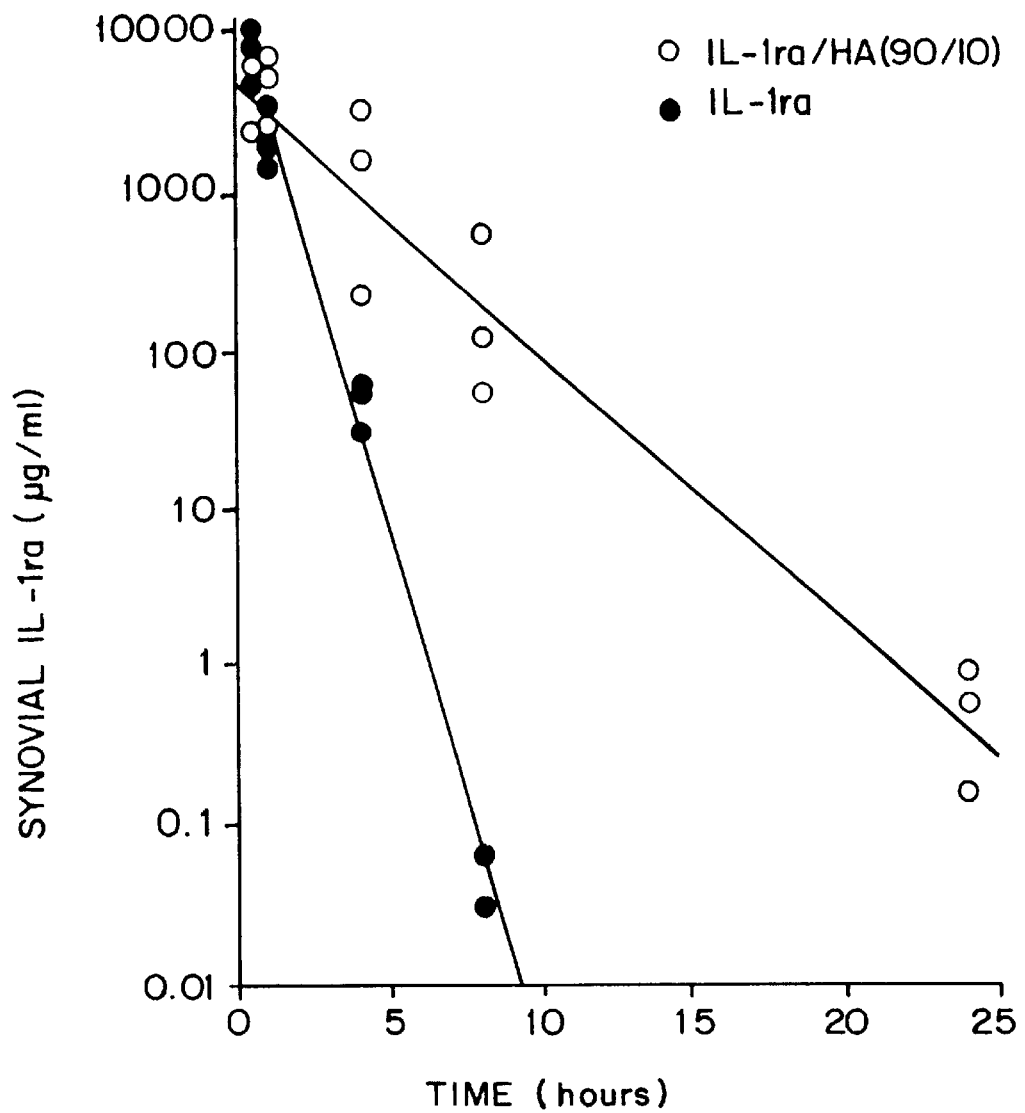
FIG. 3 shows the concentration of IL-1ra in recovered synovial fluid of rabbits after intra-articular injection of either IL-1ra alone or IL-1ra mixed with hyaluronic acid.

IL-1ra was formulated in 2% hyaluronic acid, as described above, and was injected intra-articularly into the hind knees of rabbits. At various times after injection, the animals were sacrificed and the knees lavaged with PBS to recover the synovial fluid. The concentration of IL-1ra (µg/ml) in the recovered synovial fluid was determined by ELISA (Quantikine™, human IL-1ra immunoassay, R&D Systems) according to the manufacturer's specifications. The data are shown in Table 4 and FIG. 3.

TABLE 4

Joint Half-life of IL-1ra Formulations in Hind Knees of Rabbits after Intra-articular Injection

| Time after Injection (Hours) | IL-1ra alone | IL-1ra (100 mg/ml)/ hyaluronic acid (2% w/v) |
|---|---|---|
| 0.5 | 2280 | 2440 |
| 0.5 | 11000 | 6200 |
| 0.5 | 5000 | 2410 |

TABLE 4-continued

Joint Half-life of IL-1ra Formulations in Hind Knees of Rabbits after Intra-articular Injection

| Time after Injection (Hours) | IL-1ra alone | IL-1ra (100 mg/ml)/ hyaluronic acid (2% w/v) |
|---|---|---|
| 0.5 | 8090 | ND* |
| 1 | 1400 | 5150 |
| 1 | 3450 | 6830 |
| 1 | 3090 | 7180 |
| 1 | 1840 | 2620 |
| 4 | 56.98 | 224 |
| 4 | 31.24 | 1600 |
| 4 | 62.43 | 3250 |
| 4 | ND* | 237 |
| 8 | 0.0641 | 575 |
| 8 | 0.0312 | 55.98 |
| 8 | ND* | 125 |
| 8 | ND* | ND* |
| 24 | ND* | 0.5644 |
| 24 | ND* | 0.1539 |
| 24 | ND* | 0.8852 |

*No data presented.

This data shows that the hyaluronic acid formulation of IL-1ra is capable of prolonged release of intact IL-1ra into the synovial fluid after intra-articular injection.

Example 4

Rats were immunized on day 0 and day 7 with bovine type II collagen. Arthritis developed starting on days 12–13. IL-1ra/hyaluronic acid formulations were prepared as described above (100 mg/ml IL-1ra in 2% hyaluronic acid (w/v)) and administered to arthritic rats. Rats (8 animals/ group) were injected intra-articularly with either hyaluronic acid (50 µl/knee; 1 mg hyaluronic acid total) or IL-1ra/ hyaluronic acid (50 µl/knee; 5 mg IL-1ra/1 mg hyaluronic acid) on days 15 and 18 after initial immunization. An arthritis control group received no injection. On day 20, after initial immunization, the rats were sacrificed and the knee joints collected for histologic evaluation of disease severity. As shown in Table 5 and FIG. 4: (a) treatment with IL-1ra significantly suppressed cartilage and bone damage and had a modest effect on synovitis; (b) total joint damage was reduced by 70% compared to controls and (c) treatment with hyaluronic acid alone had no beneficial effects in comparison to disease controls.

TABLE 5

IL-1ra Concentration in Synovial Fluid after Intra-articular Injection

| FORMULATIONS | SYNOVITIS | PANNUS | TOTAL CARTILAGE | BONE DAMAGE | JOINT TOTAL |
|---|---|---|---|---|---|
| Untreated | 3.25 ± 0.14 | 1.5 ± 0.16 | 17.69 ± 2.27 | 1.44 ± 0.16 | 23.88 ± 2.57 |
| hyaluronic acid (2% w/v) | 2.88 ± 0.39 | 1.44 ± 0.22 | 16.88 ± 3.14 | 1.31 ± 0.25 | 22.5 ± 3.87 |
| IL-1ra (100 mg/ml)/ hyaluronic acid (2% w/v) | 2.06 ± 0.28 | 0.5 ± 0.18 | 4.69 ± 1.77 | 0.19 ± 0.14 | 7.53 ± 2.33 |

While the present invention has been described above both generally and in terms of preferred embodiments, it is understood that other variations and modifications will occur to those skilled in the art in light of the description above.

What is claimed is:

1. A pharmaceutical composition comprising synergistic amounts of a hyaluronan or a salt thereof, and an interleukin-1 (IL-1) receptor antagonist (IL-1ra), wherein said IL-1ra comprises all or an IL-1 inhibitory fragment of an amino acid having a sequence of SEQ ID NO:2, or a sequence which is at least about 70% homologous to said amino acid sequence.

2. The composition of claim 1, wherein said IL-1ra is produced by recombinant DNA methods.

3. The pharmaceutical composition of claim 2, wherein said hyaluranon is hyaluronic acid.

4. The pharmaceutical composition of claim 2, wherein said IL-1ra comprises all or an IL-1 inhibitory fragment of an amino acid having a sequence of SEQ ID NO:2, or a sequence which is at least about 80% homologous to said amino acid sequence.

5. The pharmaceutical composition of claim 2, wherein said IL-1ra comprises all or an IL-1 inhibitory fragment of an amino acid having a sequence of SEQ ID NO:2, or a sequence which is at least about 90% homologous to said amino acid sequence.

6. The pharmaceutical composition of claim 2, wherein said IL-1ra comprises all or an IL-1 inhibitory fragment of an amino acid having a sequence of SEQ ID NO:2, or a sequence which is at least about 95% homologous to said amino acid sequence.

7. The pharmaceutical composition of claim 2, wherein said IL-1ra comprises all or an IL-1 inhibitory fragment of an amino acid having a sequence of SEQ ID NO:2.

8. The pharmaceutical composition of claim 2, wherein said IL-1ra comprises an amino acid having a sequence of SEQ ID NO:2.

9. The composition of claim 8, wherein said IL-1ra is glycosylated.

10. The composition of claim 8, wherein said IL-1ra is non-glycosylated.

11. The composition of claim 8, wherein said IL-1ra is methionyl IL-1ra.

12. The composition of claim 8, wherein the IL-1ra is present in a range of 0.1–200 mg/ml.

13. The pharmaceutical composition of claim 8, wherein the hyaluronan is present in a range of 0.1–5% w/v.

14. The pharmaceutical composition of claim 3, wherein said IL-1ra is conjugated to a dextran.

15. The pharmaceutical composition of claim 8, wherein said IL-1ra is conjugated to a dextran.

16. The pharmaceutical composition of claim 1, wherein the IL-1ra is present in a range of 0.1–200 mg/ml.

17. The pharmaceutical composition of claim 1, wherein the hyaluronan is present in a range of 0.05–5% w/v.

18. The pharmaceutical composition of claim 8, wherein the hyaluronan is present in a range of 0.05–5% w/v.

19. The pharmaceutical composition of claim 8, wherein the hyaluronan is present in a range of 0.1–4% w/v.

20. The pharmaceutical composition of claim 8, wherein the hyaluronan is present in a range of 1–3% w/v.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 462 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..462

(ix) FEATURE:
        (A) NAME/KEY: misc_feature
        (B) LOCATION: 1..3
        (D) OTHER INFORMATION: /note= "Initial methionine is
            optional."

(xi) SEQUENCE DESCRIPTION: SEQ ID NO:1:

```
ATG CGA CCC TCT GGG AGA AAA TCC AGC AAG ATG CAA GCC TTC AGA ATC        48
Met Arg Pro Ser Gly Arg Lys Ser Ser Lys Met Gln Ala Phe Arg Ile
 1               5                  10                  15

TGG GAT GTT AAC CAG AAG ACC TTC TAT CTG AGG AAC AAC CAA CTA GTT        96
Trp Asp Val Asn Gln Lys Thr Phe Tyr Leu Arg Asn Asn Gln Leu Val
             20                  25                  30

GCT GGA TAC TTG CAA GGA CCA AAT GTC AAT TTA GAA GAA AAG ATA GAT       144
Ala Gly Tyr Leu Gln Gly Pro Asn Val Asn Leu Glu Glu Lys Ile Asp
         35                  40                  45

GTG GTA CCC ATT GAG CCT CAT GCT CTG TTC TTG GGA ATC CAT GGA GGG       192
Val Val Pro Ile Glu Pro His Ala Leu Phe Leu Gly Ile His Gly Gly
     50                  55                  60

AAG ATG TGC CTG TCC TGT GTC AAG TCT GGT GAT GAG ACC AGA CTC CAG       240
Lys Met Cys Leu Ser Cys Val Lys Ser Gly Asp Glu Thr Arg Leu Gln
 65                  70                  75                  80

CTG GAG GCA GTT AAC ATC ACT GAC CTG AGC GAG AAC AGA AAG CAG GAC       288
Leu Glu Ala Val Asn Ile Thr Asp Leu Ser Glu Asn Arg Lys Gln Asp
                 85                  90                  95

AAG CGC TTC GCC TTC ATC CGC TCA GAC AGT GGC CCC ACC ACC AGT TTT       336
Lys Arg Phe Ala Phe Ile Arg Ser Asp Ser Gly Pro Thr Thr Ser Phe
            100                 105                 110

GAG TCT GCC GCC TGC CCC GGT TGG TTC CTC TGC ACA GCG ATG GAA GCT       384
Glu Ser Ala Ala Cys Pro Gly Trp Phe Leu Cys Thr Ala Met Glu Ala
        115                 120                 125

GAC CAG CCC GTC AGC CTC ACC AAT ATG CCT GAC GAA GGC GTC ATG GTC       432
Asp Gln Pro Val Ser Leu Thr Asn Met Pro Asp Glu Gly Val Met Val
    130                 135                 140

ACC AAA TTC TAC TTC CAG GAG GAC GAG TAG                               462
Thr Lys Phe Tyr Phe Gln Glu Asp Glu *
145                 150
```

(2) INFORMATION FOR SEQ ID NO:2:

(i) SEQUENCE CHARACTERISTICS:
        (A) LENGTH:  153 amino acids
        (B) TYPE: amino acid
        (D) TOPOLOGY: linear (ii) MOLECULE TYPE: protein (xi) SEQUENCE DESCRIPTION: SEQ ID NO:2:

```
Met Arg Pro Ser Gly Arg Lys Ser Ser Lys Met Gln Ala Phe Arg Ile
 1               5                  10                  15

Trp Asp Val Asn Gln Lys Thr Phe Tyr Leu Arg Asn Asn Gln Leu Val
            20                  25                  30

Ala Gly Tyr Leu Gln Gly Pro Asn Val Asn Leu Glu Glu Lys Ile Asp
        35                  40                  45

Val Val Pro Ile Glu Pro His Ala Leu Phe Leu Gly Ile His Gly Gly
    50                  55                  60

Lys Met Cys Leu Ser Cys Val Lys Ser Gly Asp Glu Thr Arg Leu Gln
65                  70                  75                  80

Leu Glu Ala Val Asn Ile Thr Asp Leu Ser Glu Asn Arg Lys Gln Asp
                85                  90                  95

Lys Arg Phe Ala Phe Ile Arg Ser Asp Ser Gly Pro Thr Thr Ser Phe
            100                 105                 110

Glu Ser Ala Ala Cys Pro Gly Trp Phe Leu Cys Thr Ala Met Glu Ala
        115                 120                 125

Asp Gln Pro Val Ser Leu Thr Asn Met Pro Asp Glu Gly Val Met Val
    130                 135                 140

Thr Lys Phe Tyr Phe Gln Glu Asp Glu
145                 150
```